(12) United States Patent
McDarby et al.

(10) Patent No.: US 11,801,009 B2
(45) Date of Patent: Oct. 31, 2023

(54) SYSTEM AND METHOD FOR DETERMINING SLEEP STAGE

(71) Applicant: RESMED SENSOR TECHNOLOGIES LIMITED, Clonskeagh (IE)

(72) Inventors: Gareth McDarby, Wicklow (IE); Emer O'Hare, Dublin (IE); Paul Phillips, Donaghadee (GB); Conor Heneghan, San Diego, CA (US); Trevor Murray, Belfast (IE)

(73) Assignee: ResMed Sensor Technologies Limited

( * ) Notice: Subject to any disclaimer, the term of this patent is extended or adjusted under 35 U.S.C. 154(b) by 627 days.

(21) Appl. No.: 16/846,959

(22) Filed: Apr. 13, 2020

(65) Prior Publication Data

US 2020/0337634 A1    Oct. 29, 2020

Related U.S. Application Data

(63) Continuation of application No. 14/429,589, filed as application No. PCT/US2013/060652 on Sep. 19, 2013, now Pat. No. 10,660,563.

(30) Foreign Application Priority Data

Sep. 19, 2012    (IE) .................................... 2012/0409

(51) Int. Cl.
*A61B 5/00*    (2006.01)
*A61B 5/05*    (2021.01)
(Continued)

(52) U.S. Cl.
CPC .............. *A61B 5/4812* (2013.01); *A61B 5/05* (2013.01); *A61B 5/0507* (2013.01);
(Continued)

(58) Field of Classification Search
CPC ....... A61B 5/05; A61B 5/0507; A61B 5/0816; A61B 5/113; A61B 5/1118; A61B 5/4812;
(Continued)

(56) References Cited

U.S. PATENT DOCUMENTS

| 4,085,740 A | 4/1978 | Allen |
| 4,228,806 A | 10/1980 | Lidow |

(Continued)

FOREIGN PATENT DOCUMENTS

| CN | 1606962 A | 4/2005 |
| JP | 2000325315 | 11/2000 |

(Continued)

OTHER PUBLICATIONS

Burioka, Naoto, et al. "Approximate entropy of human respiratory movement during eye-closed waking and different sleep stages." Chest Journal 123.1 (2003): 80-86.

(Continued)

*Primary Examiner* — Brian T Gedeon
(74) *Attorney, Agent, or Firm* — Botos Churchill IP Law LLP

(57) ABSTRACT

Methods and apparatus monitor health by detection of sleep stage. For example, a sleep stage monitor (100) may access sensor data signals related to bodily movement and/or respiration movements. At least a portion of the detected signals may be analyzed to calculate respiration variability. The respiration variability may include one or more of variability of respiration rate and variability of respiration amplitude. A processor may then determine a sleep stage based on one or more of respiration variability and bodily movement, such as with a combination of both. The determination of sleep stages may distinguish between deep sleep and other stages of sleep, or may differentiate between deep sleep, light sleep and REM sleep. The bodily movement and (Continued)

respiration movement signals may be derived from one or more sensors, such as non-invasive sensor (e.g., a non-contact radio-frequency motion sensor or a pressure sensitive mattress).

56 Claims, 35 Drawing Sheets

(51) Int. Cl.
*A61B 5/0507* (2021.01)
*A61B 5/08* (2006.01)
*A61B 5/113* (2006.01)
*A61M 16/00* (2006.01)
*A61B 5/11* (2006.01)

(52) U.S. Cl.
CPC ............ *A61B 5/0816* (2013.01); *A61B 5/113* (2013.01); *A61B 5/726* (2013.01); *A61B 5/7264* (2013.01); *A61B 5/7278* (2013.01); *A61M 16/0069* (2014.02); *A61B 5/1118* (2013.01); *A61B 2562/0228* (2013.01); *A61M 2205/3303* (2013.01); *A61M 2230/63* (2013.01)

(58) Field of Classification Search
CPC ..... A61B 5/726; A61B 5/7264; A61B 5/7278; A61B 2562/0228; A61B 2205/3303; A61M 16/0069; A61M 2230/63
See application file for complete search history.

(56) References Cited

U.S. PATENT DOCUMENTS

| | | | |
|---|---|---|---|
| 4,782,832 A | 11/1988 | Trimble et al. | |
| 4,944,310 A | 7/1990 | Sullivan | |
| 5,047,930 A | 9/1991 | Martens et al. | |
| 5,280,791 A | 1/1994 | Lavie | |
| 5,732,696 A | 3/1998 | Rapoport et al. | |
| 6,426,716 B1 | 7/2002 | McEwan | |
| 6,454,719 B1 | 9/2002 | Greenhut | |
| 6,532,959 B1 | 3/2003 | Berthon-Jones | |
| 6,581,594 B1 | 6/2003 | Drew et al. | |
| 6,804,405 B2 | 10/2004 | Christopoulos et al. | |
| 6,852,084 B1 | 2/2005 | Boesen | |
| 7,248,915 B2 | 7/2007 | Roennholm | |
| 7,306,567 B2 | 12/2007 | Loree et al. | |
| 7,427,270 B2 | 9/2008 | Izumi et al. | |
| 7,524,279 B2 | 4/2009 | Auphan | |
| 7,608,041 B2 | 10/2009 | Sutton | |
| 7,679,545 B2 | 3/2010 | Rausch et al. | |
| 7,898,455 B2 | 3/2011 | Rosenbury | |
| 7,952,515 B2 | 5/2011 | Mcewan | |
| 7,956,755 B2 | 6/2011 | Lee et al. | |
| 7,956,756 B2 | 6/2011 | Kubey et al. | |
| 8,026,840 B2 | 9/2011 | Dwelly et al. | |
| 8,096,960 B2 | 1/2012 | Loree et al. | |
| 8,398,538 B2 | 3/2013 | Dothie et al. | |
| 8,428,696 B2 | 4/2013 | Foo | |
| 8,454,528 B2 | 6/2013 | Yuen et al. | |
| 8,608,655 B2 | 12/2013 | Izumi | |
| 2004/0010202 A1 | 1/2004 | Nakatani | |
| 2004/0193068 A1 | 9/2004 | Burton et al. | |
| 2004/0210155 A1 | 10/2004 | Takemura | |
| 2005/0080349 A1 | 4/2005 | Okada et al. | |
| 2006/0169282 A1 | 8/2006 | Izumi et al. | |
| 2006/0184056 A1 | 8/2006 | Chazal | |
| 2006/0293602 A1 | 12/2006 | Clark | |
| 2007/0100666 A1* | 5/2007 | Stivoric ................ | A63F 13/211 374/E1.002 |
| 2008/0033306 A1 | 2/2008 | Joeken | |
| 2008/0306351 A1 | 12/2008 | Izumi | |
| 2009/0044808 A1 | 2/2009 | Guney et al. | |
| 2009/0050156 A1 | 2/2009 | Ng et al. | |
| 2009/0131803 A1 | 5/2009 | Heneghan et al. | |
| 2009/0203972 A1 | 8/2009 | Heneghan et al. | |
| 2010/0000534 A1 | 1/2010 | Kooij et al. | |
| 2010/0014725 A1 | 1/2010 | Watson | |
| 2010/0016694 A1 | 1/2010 | Martin et al. | |
| 2010/0152546 A1 | 6/2010 | Behan et al. | |
| 2010/0152600 A1 | 6/2010 | Droitcour | |
| 2011/0015495 A1 | 1/2011 | Dothie et al. | |
| 2011/0046498 A1* | 2/2011 | Klap ................... | A61B 5/6887 600/534 |
| 2011/0112425 A1 | 5/2011 | Muhlsteff et al. | |
| 2011/0124979 A1 | 5/2011 | Heneghan et al. | |
| 2012/0130445 A1 | 5/2012 | Lee et al. | |
| 2012/0179061 A1 | 7/2012 | Ramanan et al. | |
| 2012/0245479 A1 | 9/2012 | Ganesh et al. | |
| 2013/0006124 A1 | 1/2013 | Eyal et al. | |
| 2013/0053653 A1 | 2/2013 | Cuddihy et al. | |
| 2013/0066226 A1 | 3/2013 | Leonardo et al. | |
| 2013/0135137 A1 | 5/2013 | Mulder et al. | |
| 2013/0172770 A1 | 7/2013 | Muehlsteff | |

FOREIGN PATENT DOCUMENTS

| | | | | |
|---|---|---|---|---|
| JP | 2003088512 A | 3/2003 | | |
| JP | 2007289660 | 11/2007 | | |
| JP | 2009538720 A | 11/2009 | | |
| JP | 2011015887 | 1/2011 | | |
| JP | 2011160852 A | 8/2011 | | |
| JP | 2012161641 A | 8/2012 | | |
| WO | 1998004310 A1 | 2/1998 | | |
| WO | 1998034665 A1 | 8/1998 | | |
| WO | 2000078381 | 12/2000 | | |
| WO | 2004073778 A1 | 9/2004 | | |
| WO | 2004112606 A1 | 12/2004 | | |
| WO | 2005063328 A1 | 7/2005 | | |
| WO | WO-2006066337 A1 * | 6/2006 | ........... | A61B 5/0826 |
| WO | 2006074513 A1 | 7/2006 | | |
| WO | 2006130903 A1 | 12/2006 | | |
| WO | 2007143535 A2 | 12/2007 | | |
| WO | 2008096307 A1 | 8/2008 | | |
| WO | 2008098943 A2 | 8/2008 | | |
| WO | 2009052560 A1 | 4/2009 | | |
| WO | 2009124297 A1 | 10/2009 | | |
| WO | WO-2009124297 A1 * | 10/2009 | ........... | A61B 5/0022 |
| WO | 2010048310 A1 | 4/2010 | | |
| WO | 2010132850 A1 | 11/2010 | | |
| WO | 2010135785 A1 | 12/2010 | | |
| WO | 2011006199 A1 | 1/2011 | | |
| WO | 2011019091 A1 | 2/2011 | | |
| WO | 2012073183 A1 | 6/2012 | | |
| WO | 2013009988 A1 | 1/2013 | | |
| WO | 2013093712 A1 | 6/2013 | | |

OTHER PUBLICATIONS

De Chazal, Philip, et al. "Assessment of sleep/wake patterns using a non-contact biomotion sensor." Engineering in Medicine and Biology Society, 2008. EMBS 2008. 30th Annual International Conference of the IEEE. IEEE, 2008.
Extended European Search Report for Application No. 1383835.8 dated Apr. 22, 2016.
International Search Report and Written Opinion for Application No. PCT/US2013/60652 dated Feb. 7, 2014.
Japanese Office Action dated Jul. 7, 2017 to JP Patent Application No. 2015-533189.
Non-Final Office Action issued in corresponding U.S. Appl. No. 14/429,589 dated Jul. 3, 2019.
Rostig, MD, Sven et al., "Nonrandom Variability of Respiration During Sleep in Healthy Humans." Sleep, vol. 28, No. 5, 2005.
U.S. Non-Final Office Action issued in corresponding U.S. Appl. No. 14/031,553 dated Oct. 3, 2018.
U.S. Office Action dated Jan. 18, 2018 for U.S. Appl. No. 14/429,589.
U.S. Office Action dated Dec. 18, 2017 for U.S. Appl. No. 14/031,553.

(56) References Cited

OTHER PUBLICATIONS

Office Action for Japanese Patent Application No. 2020-126540, dated Jul. 30, 2021.

* cited by examiner

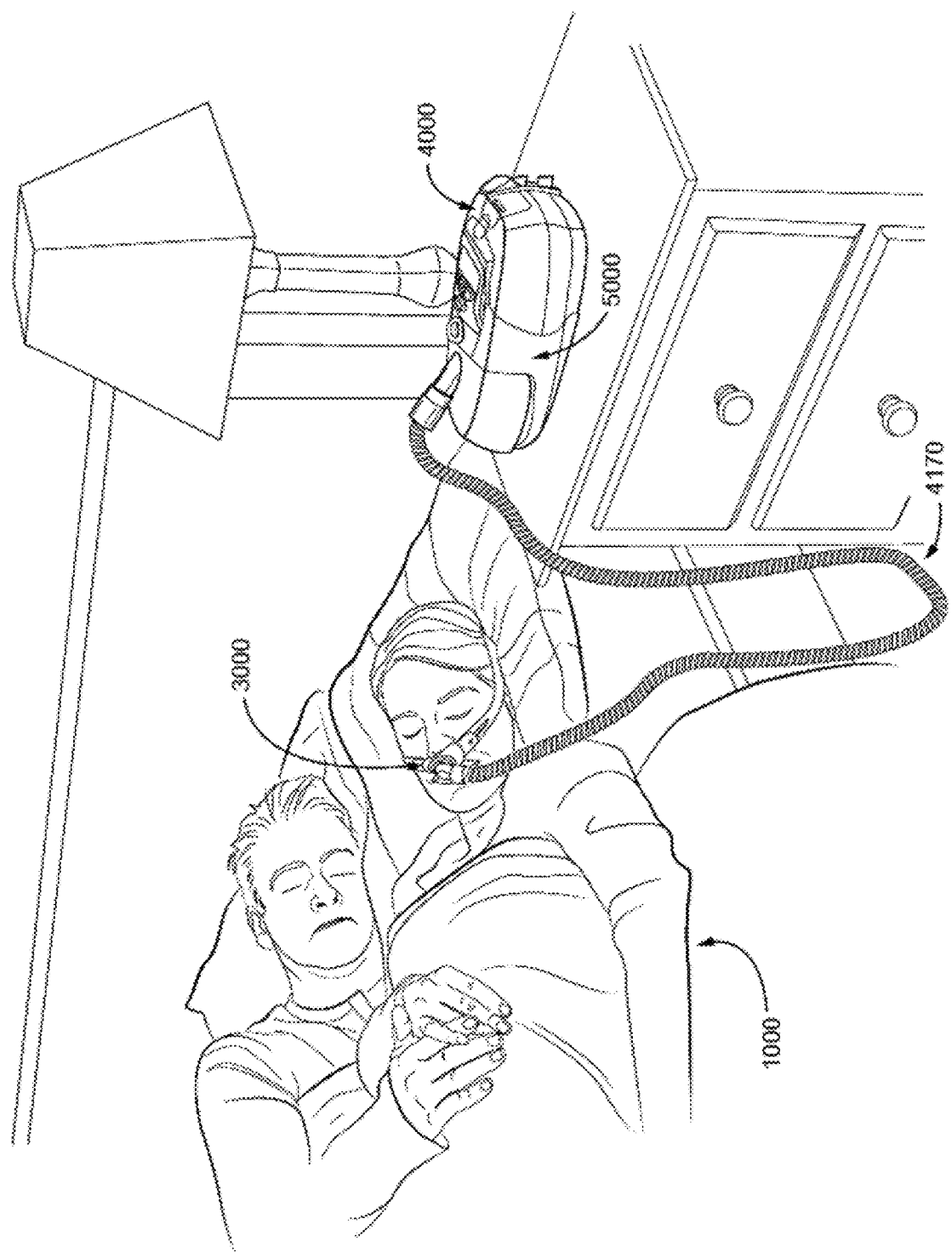

SYSTEM AND METHOD FOR DETERMINING SLEEP STAGE

1 CROSS REFERENCE TO RELATED APPLICATIONS

This application is a continuation of U.S. patent application Ser. No. 14/429,589 filed on Jun. 23, 2015, which is a national phase entry under 35 U.S.C. § 371 of International Application No. PCT/US2013/60652 filed Sep. 19, 2013, published in English, which claims priority to Irish Preliminary Patent Application No. 2012/0409 filed Sep. 19, 2012, the disclosures of all of which are incorporated herein by reference.

2 BACKGROUND OF THE TECHNOLOGY

2.1 Field of the Technology

The present technology relates to the determining of sleep stage of humans such as using respiration and movement signals and may be useful, for example, in the assessment of sleep architecture or the quality of sleep. The technology may be implemented in conjunction with devices for the diagnosis, treatment and amelioration of respiratory disorders, and to procedures to prevent respiratory disorders. Thus, the present technology may relate to medical devices, and their use for treating respiratory disorders and for preventing respiratory disorders.

2.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

2.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

| Table of noise of prior masks (ISO 17510-2: 2007, 10 cmH$_2$O pressure at 1 m) | | | | |
|---|---|---|---|---|
| Mask name | Mask type | A-weighted sound power level dbA (uncertainty) | A-weighted sound pressure dbA (uncertainty) | Year (approx.) |
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cmH$_2$O)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4 PAP Device

The air at positive pressure is typically supplied to the airway of a patient by a PAP device such as a motor-driven blower. The outlet of the blower is connected via a flexible delivery conduit to a patient interface as described above.

2.2.5 Sleep Detection

Sleep information may be useful for treating and/or diagnosing respiratory issues or may simply be useful for monitoring health. Currently, human sleep stages are typically determined using a laboratory based measurement called polysomnography. In polysomnography, it is typical for several electroencephalogram (EEG) readings to be taken (EEGs are the microvolt potentials generated by brain activity that can be measured at the scalp using electrodes), in addition to other parameters such as respiration, electrocardiogram (ECG), leg movements, and electro-oculograms (EOG). Based on work originally pioneered by Rechtschaffen and Kales (R&K), it is now conventional to score human sleep in 30-second epochs, and to label these epochs using sleep stage labels.

At present, the American Academy of Sleep Medicine defines the stages of sleep as:

Wake—this is when a person is fully awake, and is characterized by a positive dominant rhythm in the occipital EEG channel (when eyes are closed), typically in the range 8-14 Hz (often referred to as alpha waves)

Stage N1—this is the lightest stage of sleep, and is characterized by the appearance of some low amplitude waves at multiple frequencies interspersed with the alpha waves for >50% of an epoch. There may also be sharp vertex waves, some slow eye movements on the EOG and/or an overall lowering of the frequency of EEG.

Stage N2—this is a slightly deeper stage of sleep, and is marked by the appearance of sleep spindles and K-complexes, on a background of mixed frequency signals. Sleep spindles are bursts of higher frequency activity (e.g. >12 Hz). K-complexes are distinct isolated bipolar waves lasting about 1-2 seconds.

Stage N3 is the deepest stage of sleep (in the original R&K classification, there were two distinct stages called Stage 3 and Stage 4). This is characterised by the appearance of slow waves (e.g., 1-2 Hz frequency) for at least 20% of an epoch.

Stage R (REM)—this is rapid eye movement sleep, and is apparent through the presence of distinct activity in the EOG signal. The EEG signals recorded are typically quite similar to Stage N1 or even wake.

An automated system from scoring polysomnogram data is discussed in U.S. Pat. No. 5,732,696 to Rapoport et al. The system uses a computer to look for elemental patterns in the PSG data (such as the sleep spindles described above), and then uses a probabilistic weighting to score each epoch. However this approach to the problem of determining sleep stages is limited by the technical difficulty of measurement of a full set of polysomnogram signals, and hence is difficult and cumbersome to implement for more than a single night.

A number of systems have provided alternative solutions to the problem of determining sleep stage. One approach is to use actigraphy, in which small motion sensors (e.g., accelerometers) are worn by a user, typically in a wristwatch configuration. However, such systems have the disadvantage that they can only distinguish between sleep and wake, with poor accuracy in patients with sleep disorders.

US2006/0184056 (Heneghan et al) describes a sleep monitoring system which uses an ECG signal which is processed to determine a status for each epoch, either apneic or normal.

WO2007/143535 (Heneghan et al) describes a system for monitoring physiological signs such as sleep state by monitoring motion, breathing, and heart rate signals obtained in a non-contact fashion. A classifier model is applied to the streams of data.

A system which combines ECG and respiration methods to determine simplified sleep stage is described in US20090131803 (Heneghan et al). This combines signal characteristics derived from cardiogram and respiration signals, such as the amplitude modulation of the ECG signal and the dominant respiratory frequency in order to distinguish sleep from wakefulness.

WO2004112606 (Heneghan et al) describes a method of detecting sleep apnea using trans-cervical bioimpedance measurements.

US2011/0124979 (Heneghan et al) describes an approach to sleep monitoring using ECG and photoplethysmogram (PPG) data. These may be sensed using a Holter monitor and a pulse oximeter which are wearable in an ambulatory manner.

An approach in which cardiac R-R wave intervals are used to designate sleep as REM or non-REM is discussed in U.S. Pat. No. 5,280,791 to Lavie. A power spectrum of the cardiac R-R interval is calculated in order to determine the stages of sleep.

A US application 2013/0006124, to Eyal and Baharav, discusses the use of a non-ECG device such as a plethysmograph, radar, microphone, accelerometer etc., for measuring patient's heartbeats, analysing the inter-beat intervals and determining if the subject is in a sleep stage (light sleep, slow wave sleep, REM).

3 BRIEF SUMMARY OF THE TECHNOLOGY

This disclosure has application in the field of sleep research and in providing quality-of-life metrics to individual users.

The present technology is directed towards providing health or medical devices for detection of sleep related information and may optionally be used in the diagnosis, amelioration, treatment, or prevention of respiratory disorders having one or more of improved comfort, cost, efficacy, ease of use and manufacturability.

For example, this disclosure provides various embodiments and aspects of an apparatus, system and method for determining sleep stage in a non-contact manner.

In one aspect, an apparatus, system, and method is provided for deriving the sleep stage of a human subject based solely on measurement of the bodily movement and respiration movement of the subject. The sleep stages provided can distinguish between deep sleep and all other stages of sleep, or could further differentiate between deep sleep, light sleep and REM sleep. In this context, deep sleep refers to Stage N3 as defined by the American Academy of Sleep Medicine. Stage N1 and N2 are collectively referred to as "light sleep'. The bodily movement and respiration movement may be obtained through a non-invasive sensor such as a pressure sensitive mattress or a radio-frequency motion sensor. The later sensor is also a completely non-contact sensor, as the user does not have to be in mechanical contact with the sensor (In the case of the pressure sensor, some contact is necessary).

Thus, according to the current technology (a) there may be no need for any direct electrical or mechanical contact with the patient, e.g., no ECG, inductance plethysmogram or bioimpedance signals are acquired, (b) there may be no need for cardiac information to be acquired, sleep state estimation is performed solely on movement and respiration signals. Thus, the proposed technology overcomes or ameliorates at least some of the issues with the prior art or proposes a useful alternative.

In one embodiment, a radio-frequency sensor unit can be placed on a bedside table near a subject's bed, while they sleep. The sensor may be range gated so that its operation can be limited to a specific distance from the sensor, providing it with a required spatial resolution. The sensor unit may communicate with a processor and a display and, in one aspect, the sensor, the processor, and the display may be physically implemented in the same unit. The processor may be used to extract information about breathing and motion, and higher order information such as the sleep stage. A display may be configured to provide feedback to the user, typically at the end of the night, such as displaying a sequence of the overnight sleep stages. Feedback can also be provided real time such that to allow using the presence of sleep to control environmental factors such as the ambient temperature, the ambient light level, the ambient noise or ambient odour. The feedback could also be used to control electronic devices such as radios, televisions or other entertainment devices. In one aspect, a complete system may include one or more of the following: A motion sensor (for detection of general bodily movement and respiration); a processing capability (to derive signals directly related to breathing and motion, and hence to derive sleep stage); a display capability (to provide visual feedback); a lighting and/or light controlling capability (to alter room light), an auditory capability (to provide acoustic feedback, e.g., a white noise generator whose amplitude varies with sleep stage); and/or a communications capability (wired or wireless) to transmit acquired data to a separate unit. The same or separate unit may be configured to carry out the processing, display, lighting and auditory functions mentioned above. The separate unit could be a local device such as a cellular phone or tablet computer, or it could be a remote computer.

In one or more embodiments, the disclosed system measures the respiration and/or movement signal by way of one or more sensors configured to receive a reflected radio-frequency signal off a living subject. A processor is configured to analyze the reflected signal to determine a measurement of movement and respiration, and hence sleep stage; and a display arranged to provide selected information relating to one or more of breathing, movement and sleep stage to a user of the system. The system may further comprise a transmitter that generates the radio frequency signals that are reflected off the living subject, and the power levels emitted by the system are safe for continuous use with humans.

In another embodiment, a method for measuring and analyzing respiration, cardiac activity, and bodily movement includes receiving radio-frequency signals reflected from a human subject; analyzing the reflected signals to produce measurements relating to movement and respiration, and hence sleep stage; and providing selected information to a user of the system, which may be displayed on a screen.

In one aspect, the invention provides a method for classifying sleep stages of a subject, the method comprising:

detecting one or more signals related to bodily movement and respiration movements of the subject; and analyzing at least a portion of the detected signals to calculate the variability of the respiration rate and/or respiration amplitude; and combining the respiration variability with the bodily movement detection to determine sleep stage.

In one embodiment, the analysis determines respiration rate and respiration amplitude. A processing means is provided to take the original movement signal (the entire or raw detected movement signal) and to split it into "respiration" and "non-respiration" signals, by using frequency domain filtering (for example, most respiration effort signals are below 0.5 Hz so a low-pass filter can isolate only the respiration-related parts of the signal. The respiration rate and the respiration amplitude can then be calculated from just this part of the signal. However, the method may include analyzing the entire/raw detected signal to classify the sleep stages of the subject, since the non-respiration signal movement components typically reflect movements which are also useful to determine sleep state. Preferably, the detection of the one or more signals is performed in a non-contact manner.

In one embodiment, the method comprises the detection of the presence or absence of a person. Preferably, the analysis comprises a simplified sleep staging calculation in which the outputs are sleep or awake only. In one embodiment, detected signals are processed to estimate a respiratory rate of the subject. In one embodiment, detected signals are processed to estimate the respiratory amplitude of the subject. Preferably, an estimate of the respiratory rate is made on an epoch basis (e.g., over a 30-second epoch). In one embodiment, the analysis includes choosing a respiration stability threshold value depending on a comparison of the variation in amplitude of the measured respiratory signal with an amplitude threshold value. Preferably, the analysis includes choosing a respiration rate stability threshold value depending on a comparison of the variability of the measured respiratory rate signal with a threshold value.

In one embodiment, the analysis comprises calculating a respiration rate range for each of a number of epochs, based on the minimum and the maximum values of the respiration rates of each of the respective epochs. Preferably, the method comprises:

a. comparing the calculated respiration range with a chosen stability threshold value for the epoch; and b. classifying the epoch as a deep sleep if the calculated respiration range is smaller than the chosen stability threshold, or otherwise classifying the epoch as light sleep.

In one embodiment, a light sleep epoch is encountered, the sequence length of prior deep sleep epochs and, if the number of preceding epochs of deep sleep epochs encountered since the last light sleep epoch is less than a predetermined number, reclassifying these epoch as light sleep. In one embodiment, the predetermined number is five.

In one embodiment, the method comprises classifying periods of sleep as either deep sleep or REM sleep on the basis of the variation of the breathing rate during the period.

In one embodiment, the method includes classifying a period as either a deep sleep or a REM sleep period, based on whether a combination of features derived from spectral analysis and approximate entropy analysis for the period is smaller or larger, respectively, than a threshold value. In one embodiment, non-contact radio frequency-based sensors are used, and the analysis provides quadrature signals I and Q which represent the detected movement observed from positions 90° apart in the phase space of a transmitter.

In one embodiment, the analysis uses respiration rate variability and respiration amplitude variability to determine sleep stage. In one embodiment, the analysis uses variability of the respiration rate and amplitude to distinguish REM sleep, in which a period of relatively high variation of the breathing rate is considered as an indication of an REM sleep period, and a period of relatively low variation of the breathing rate is considered to be associated with a state of deep sleep. In one embodiment, the analysis comprises assessing the variability of a time series using the approximate entropy, which assumes lower values for predictable time-series, and higher values as the time-sequence becomes more variable. Preferably, the analysis provides a continuous respiration rate and respiration amplitude estimate, and the respiration rate is then fed into two processing blocks in segments, in which a block will output a single number for an epoch which is the approximate entropy of that segment of the signal.

In another aspect, the invention provides a system for classifying sleep stages of a subject, the system comprising:
one or more sensors configured to detect one or more signals which relate to bodily movement and respiration related movements; and a processor configured to analyze at least a portion of the detected signals to calculate the variability of the respiration rate and/or respiration amplitude; and to combine the respiration variability with the bodily movement detection to determine sleep stage.

In one embodiment, at least one of the one or more sensors is a non-contact sensor. In one embodiment, the at least one non-contact sensor is a radio frequency based sensor. In one embodiment, the at least one non-contact radio sensor is range gated.

Some versions of the present technology may involve a method of a processor of an apparatus for classifying sleep stages of a subject. The method may include accessing a plurality of signals related to bodily movement and/or respiration movements of the subject. The method may include selecting one of the plurality of signals for processing. The method may include processing the selected signal by wavelet transform. The method may include generating a mask corresponding to the transformed signal. The method may also include extracting features from the transformed signal in accordance with the mask. The method may also include classifying a sleep stage based on the extracted features.

In some cases, a processor may select the one of the plurality of signals by detecting a greatest in-band breathing power. In some cases, the method may further include with a processor extracting breath statistics from the transformed signal, and the classifying of the sleep stage may be further based on the breath statistics. The breath statistics may include one or more of a mean of breath interval, a mean of breath amplitude, variation of breath interval and variation of breath amplitude.

In some cases, the extracted features may include one or more of a power in a highest wavelet detail just above a breathing band and a power in approximation coefficients. Optionally, the generated mask may indicate noise for particular portions of the transformed signal. The generated mask may be a binary map of the transformed signal.

In some cases, the classifying may include linear discriminant analysis. The method may further include detecting a pattern of classified sleep stages and correcting an errant classification based on the detected pattern. Optionally, the method may further include displaying a classified sleep stage. The sleep stages may include a series of one or more of a wake stage, light sleep stage, a deep sleep stage and a rem sleep stage.

In some cases, the method(s) may be implemented by a system for classifying sleep stages of a subject. The system may include one or more sensors configured to detect a plurality of signals which relate to bodily movement and respiration related movements. The system may also include a processor configured to process the plurality of signals, select one of the plurality of signals for processing, process the selected signal by wavelet transform, generate a mask corresponding to the transformed signal, extract features from the transformed signal in accordance with the mask, and classify a sleep stage based on the extracted features. In some cases, the at least one of the one or more sensors is a non-contact sensor, which may be a radio frequency based sensor or one that is range gated. The system may further include a respiratory treatment apparatus. The respiratory treatment apparatus may include a flow generator adapted to couple with a patient interface. It may also include a controller configured to set an treatment operation of the flow generator. The controller may be in communication with the processor and configured to control a treatment pressure based, in part, on the determined sleep stage.

In a further aspect, the invention provides a computer readable medium comprising software code adapted to perform the steps of any of the methods as described herein in any embodiment, when executing on a digital processor.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

4.2 Therapy

4.2.1 Respiratory System

Figure 1B:
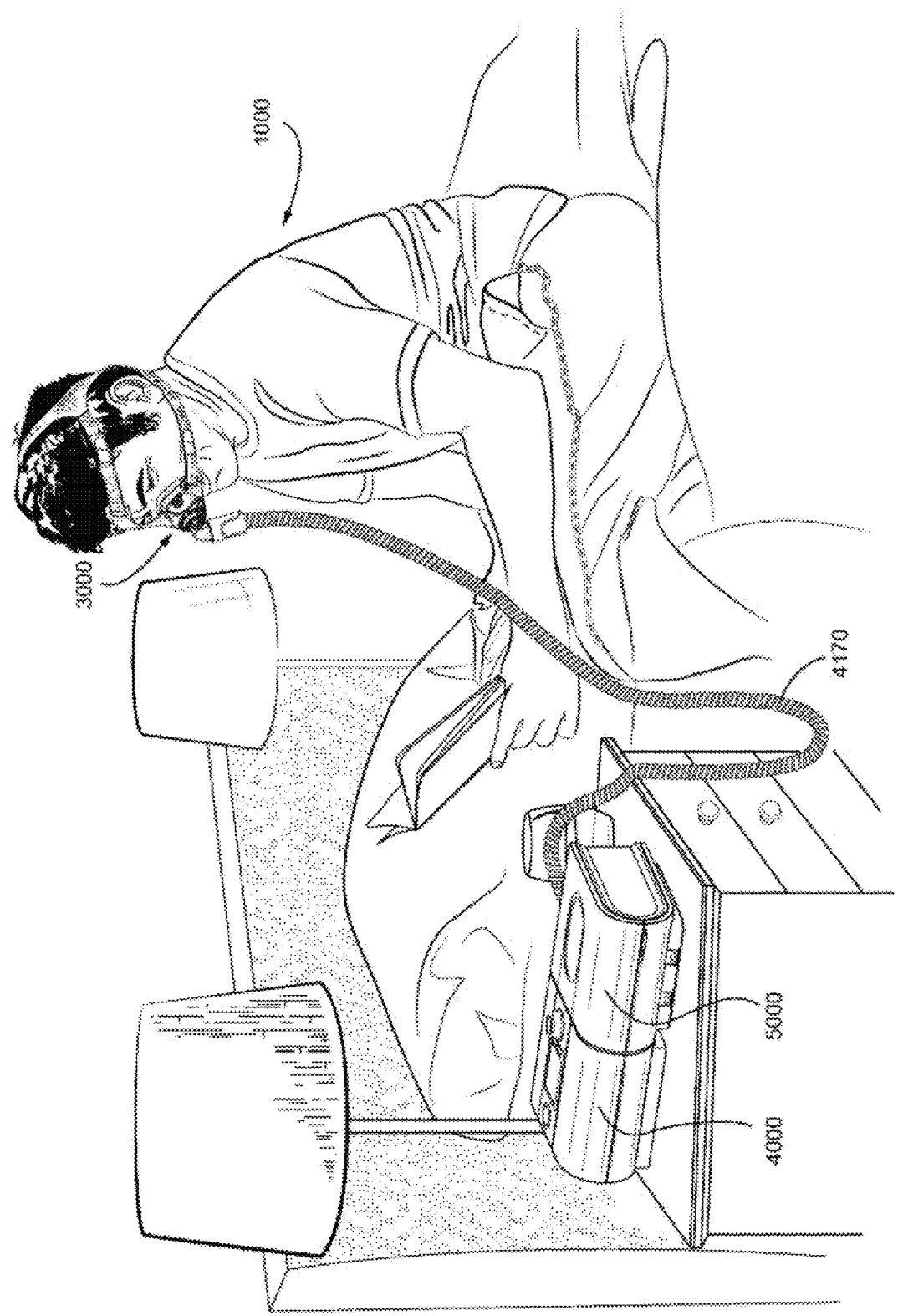
FIG. 1b shows a PAP device in use on a patient with a nasal mask.
Figure 1C:
FIG. 1c shows a PAP device in use on a patient with a full-face mask.
Figure 2A:
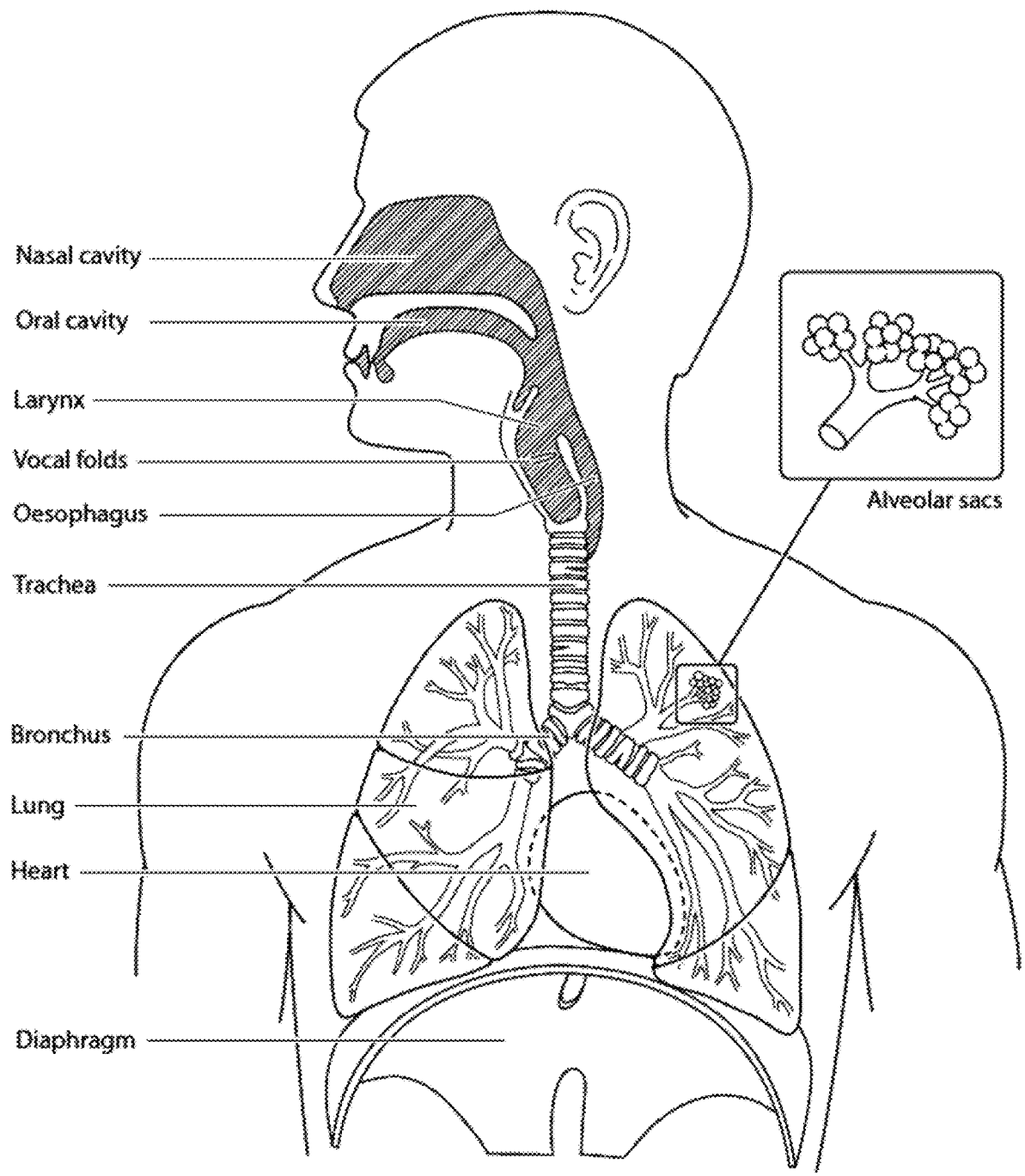

FIG. 2a shows an overview of a human respiratory system including the nasal and oral cavities, the larynx, vocal folds, oesophagus, trachea, bronchus, lung, alveolar sacs, heart and diaphragm.

Figure 2B:
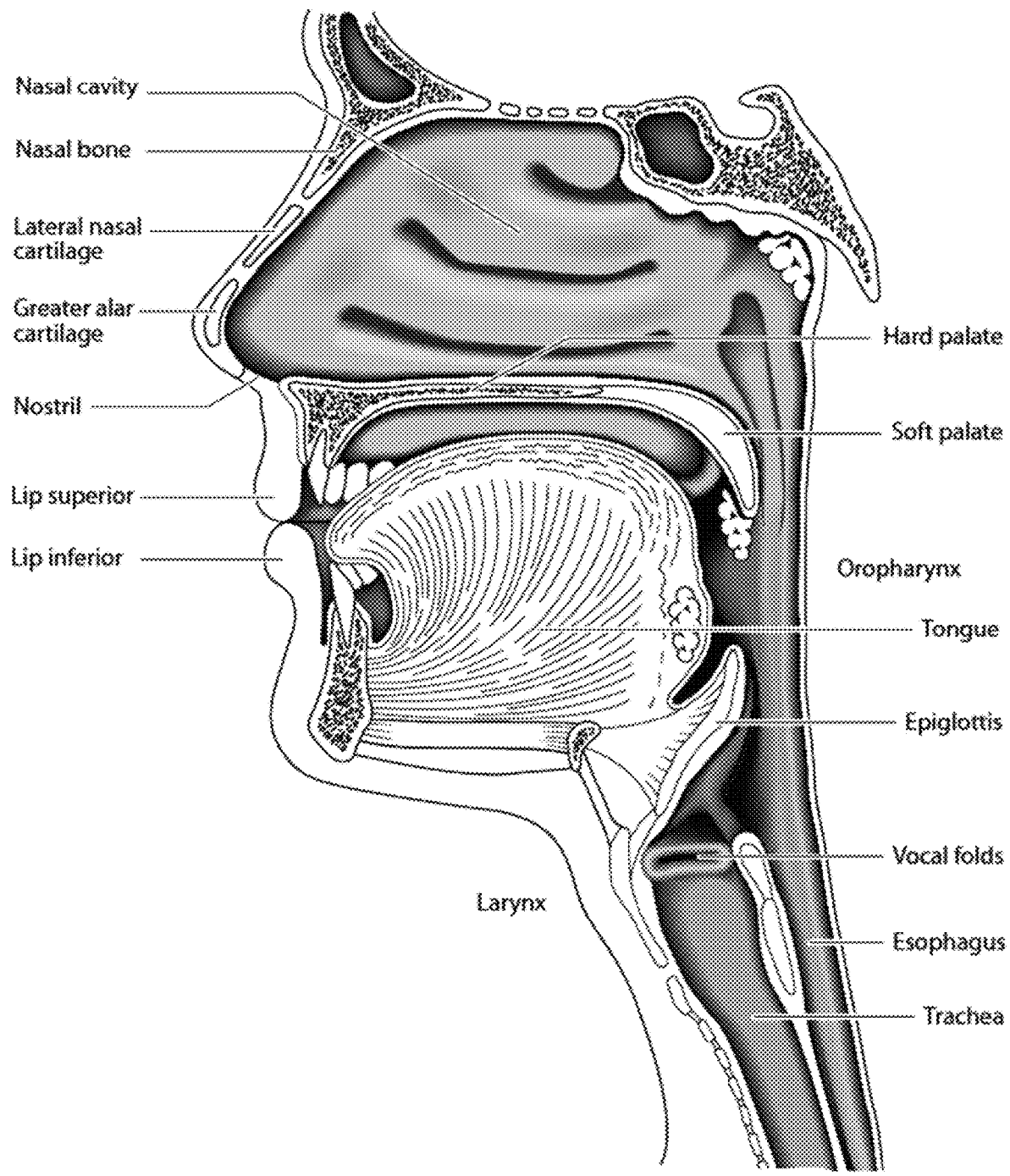

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.3 Patient Interface

Figure 3:
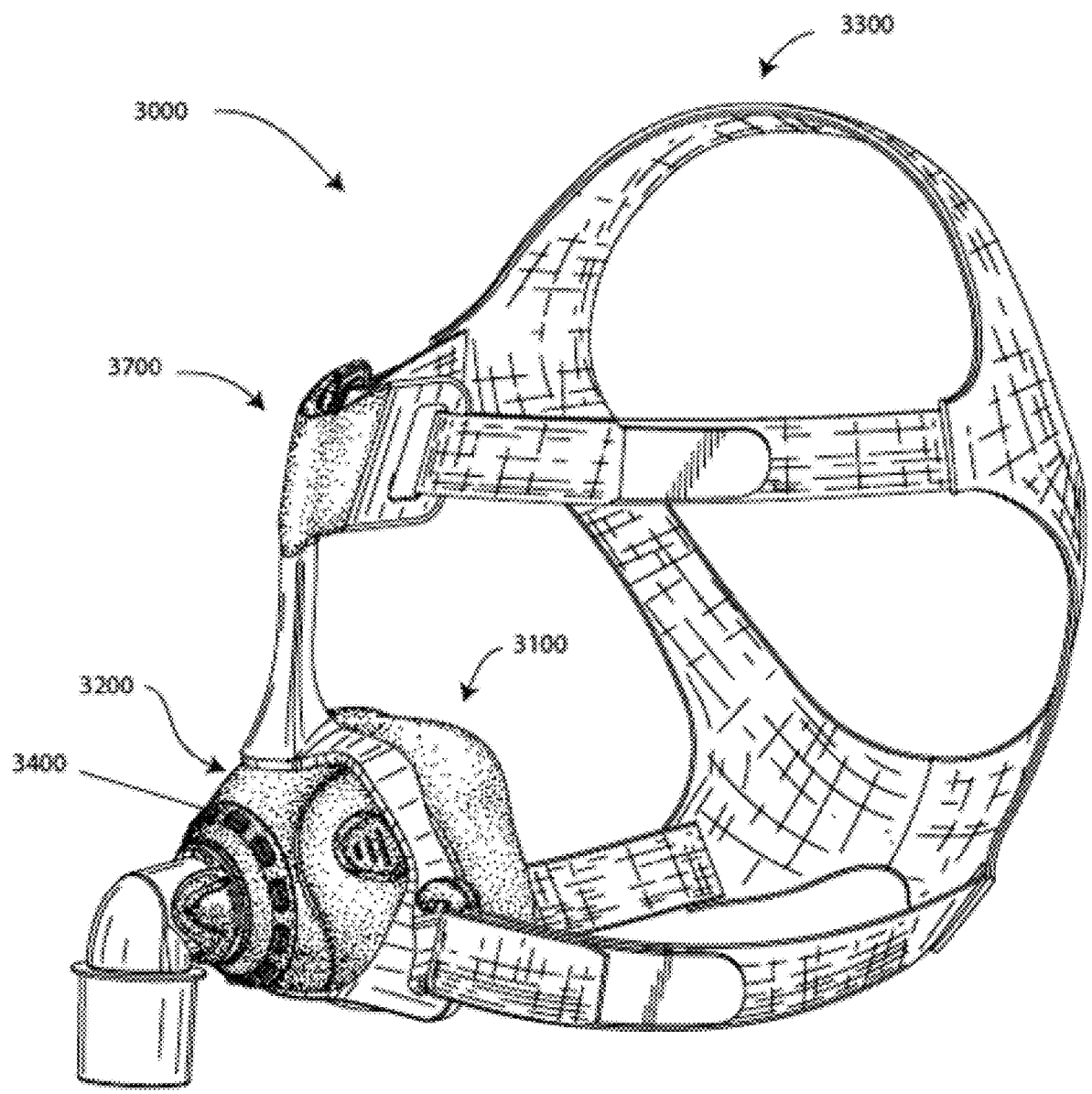

FIG. 3 shows a patient interface in accordance with one form of the present technology.

4.4 PAP Device

Figure 4A:
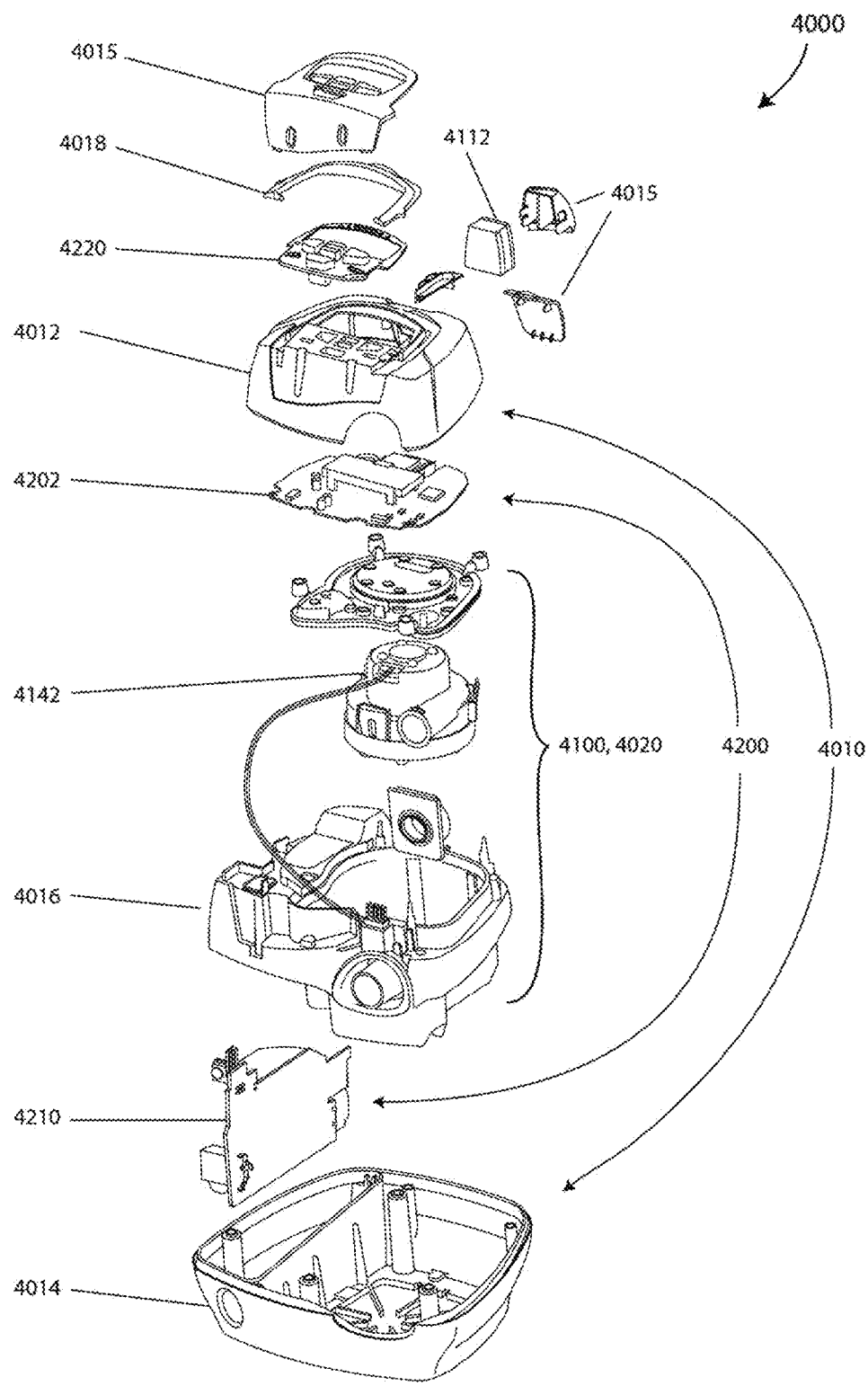

FIG. 4a shows a PAP device in accordance with one form of the present technology.

Figure 4B:
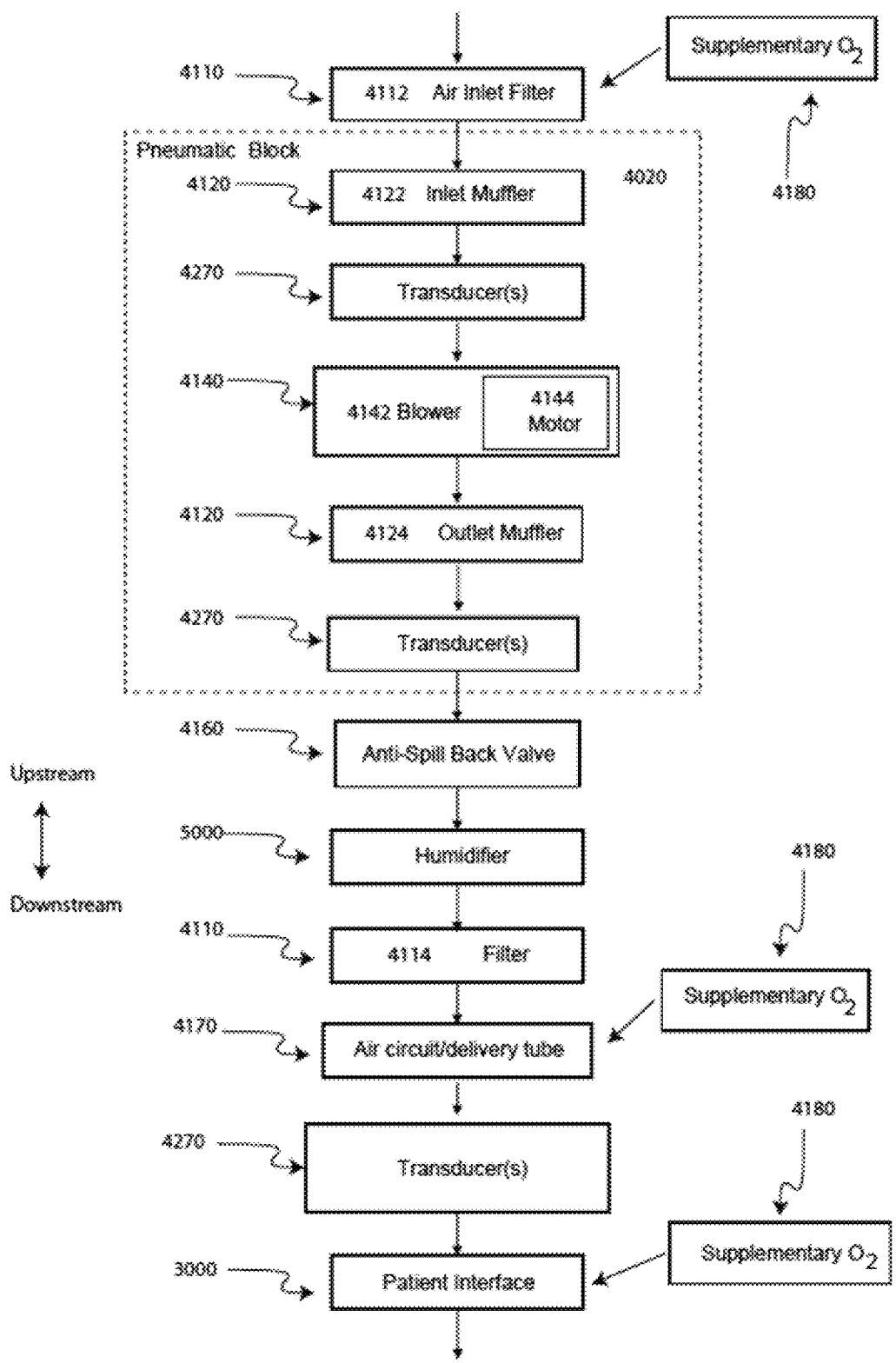

FIG. 4b shows a schematic diagram of the pneumatic circuit of a PAP device in accordance with one form of the present technology. The directions of upstream and downstream are indicated.

Figure 4C:
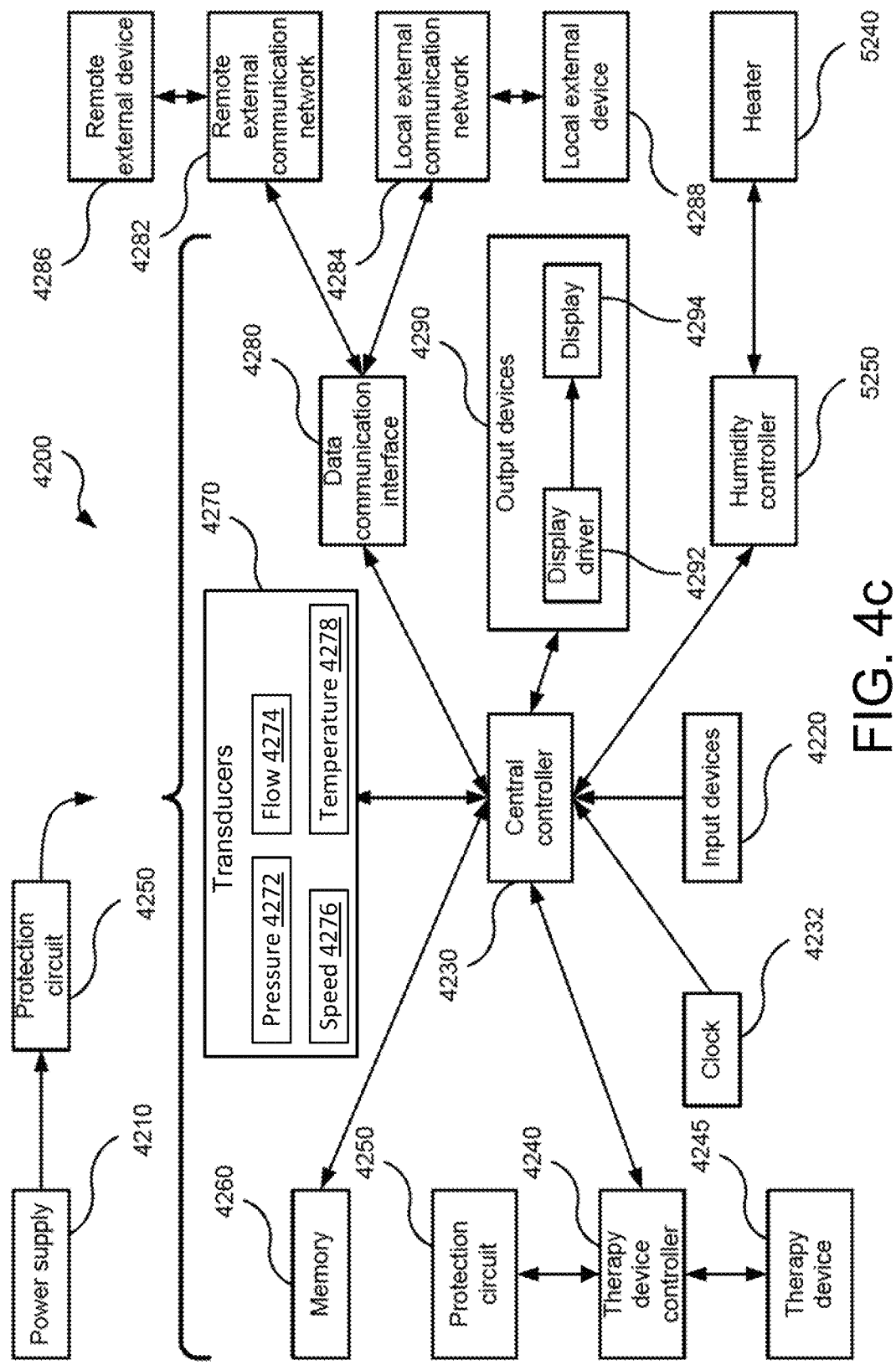

FIG. 4c shows a schematic diagram of the electrical components of a PAP device in accordance with one aspect of the present technology.

Figure 4D:
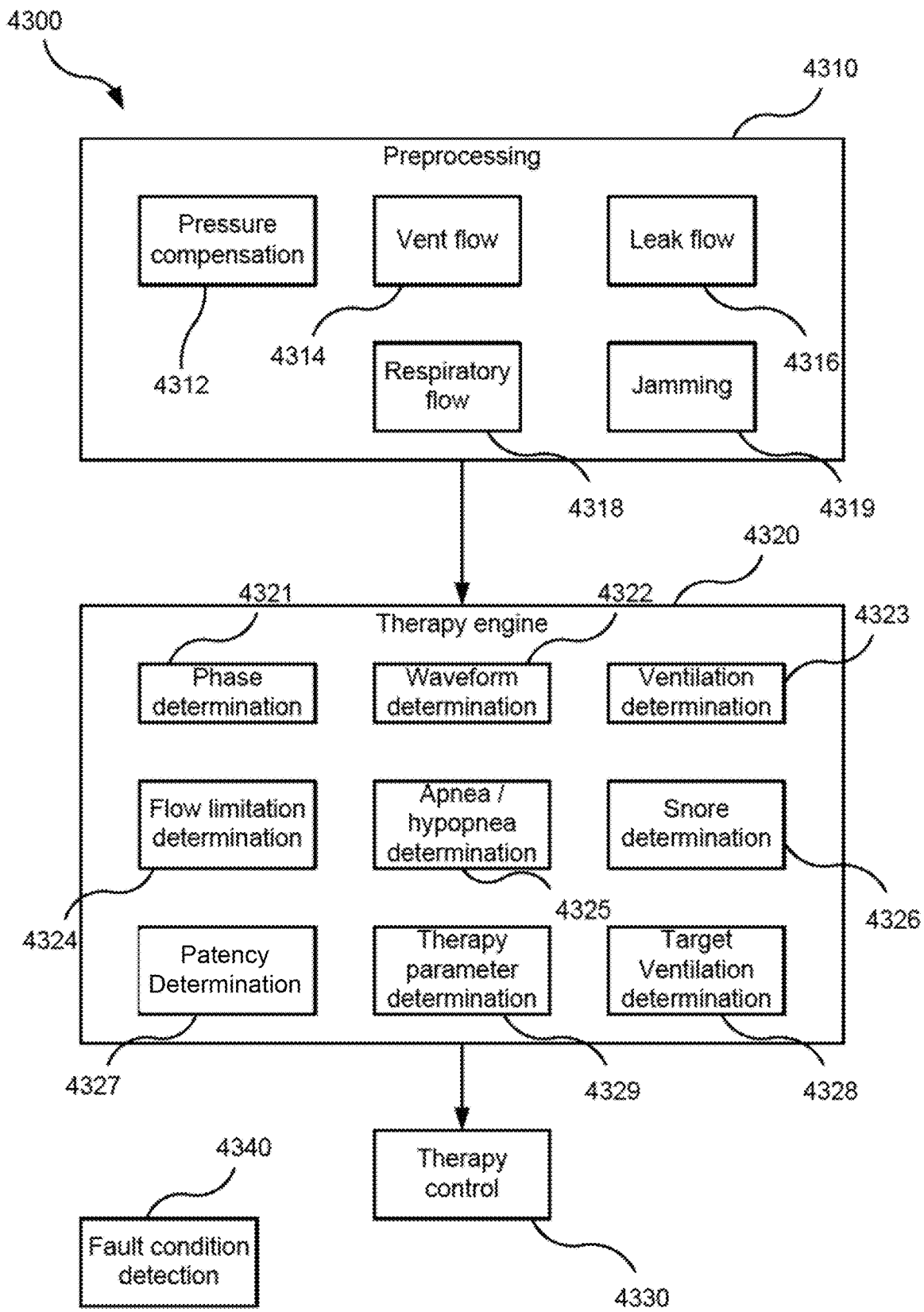

FIG. 4d shows a schematic diagram of example processes or algorithms implemented in a PAP device in accordance with an aspect of the present technology. In this figure, arrows with solid lines indicate an actual flow of information, for example via an electronic signal.

4.5 Humidifier

Figure 5:
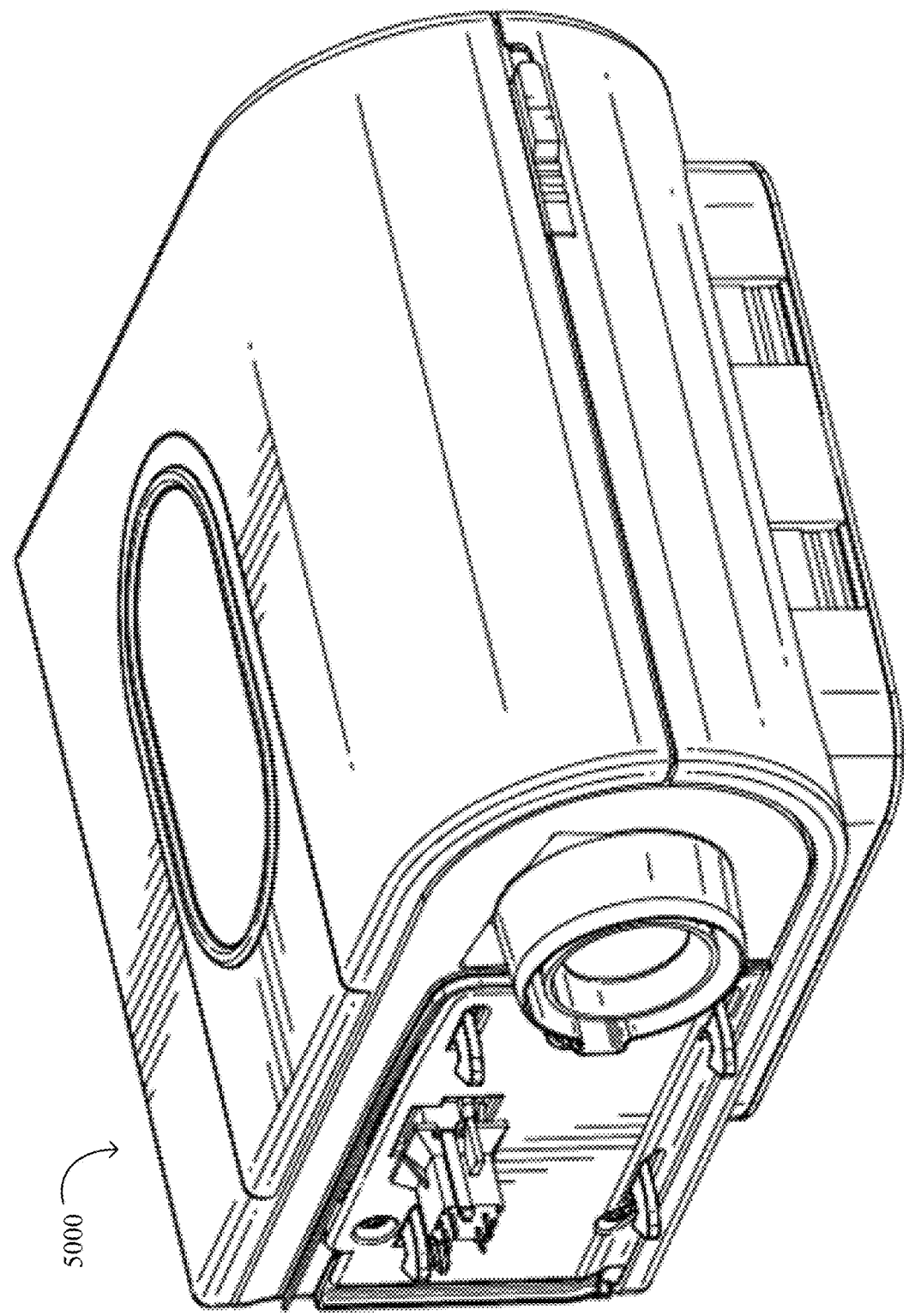

FIG. 5 shows an example humidifier in accordance with one aspect of the present technology.

4.6 Breathing Waveforms

Figure 6A:
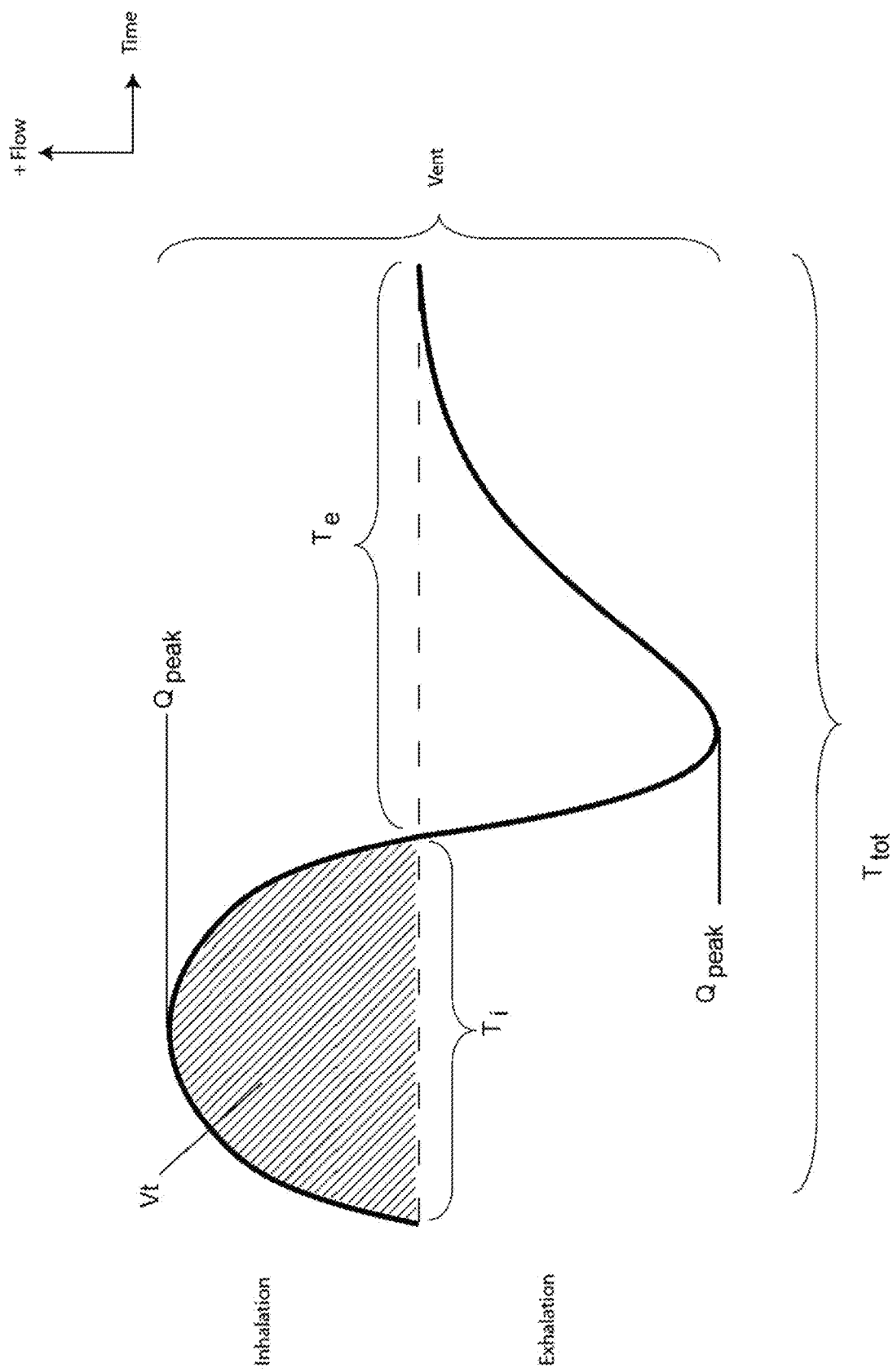

FIG. 6a shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 6B:
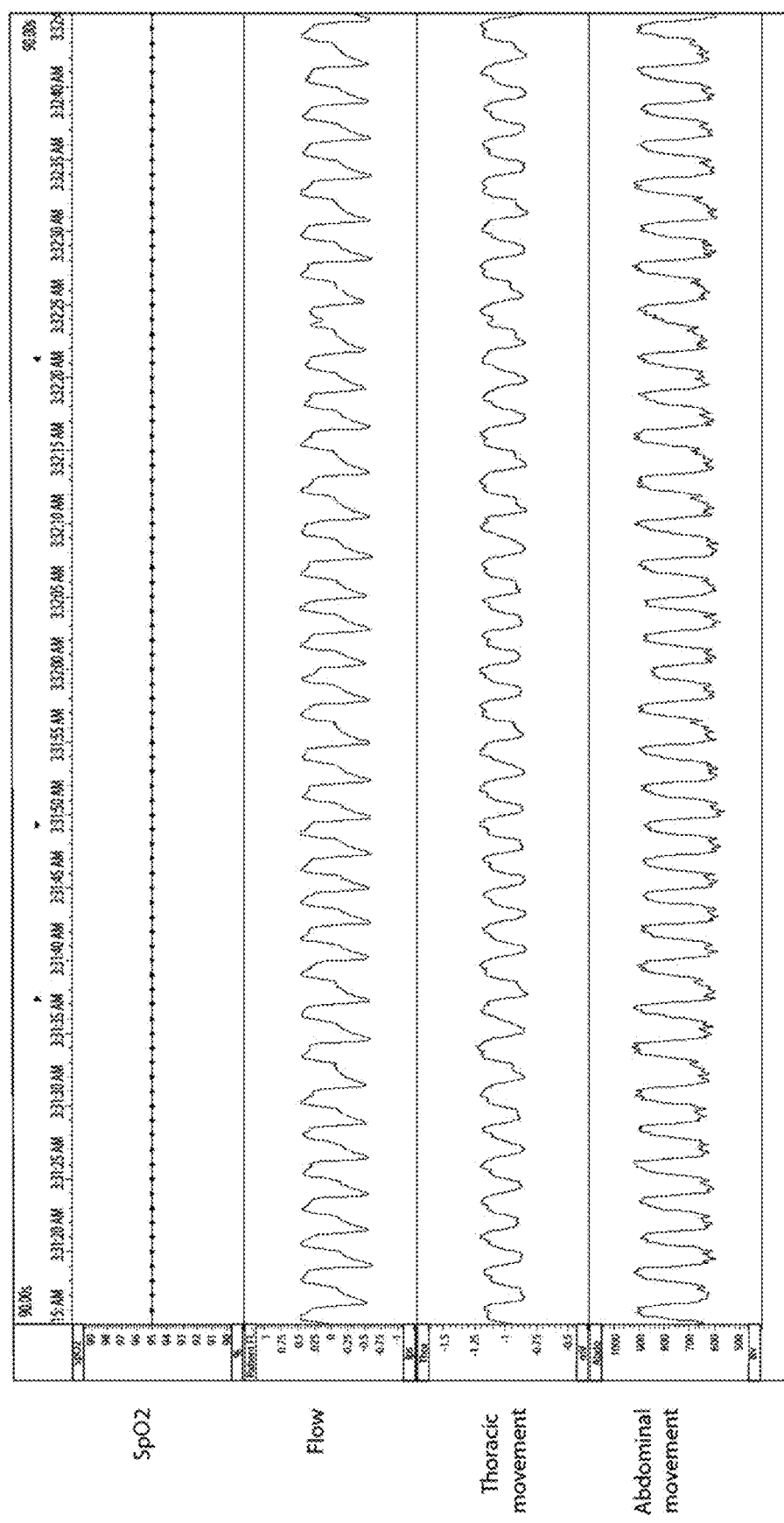

FIG. 6b shows a patient during Non-REM sleep breathing normally over a period of about ninety seconds, with about 34 breaths, being treated with Automatic PAP, and the mask pressure being about 11 cmH$_2$O. The top channel shows oximetry (SpO2), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

Figure 6C:
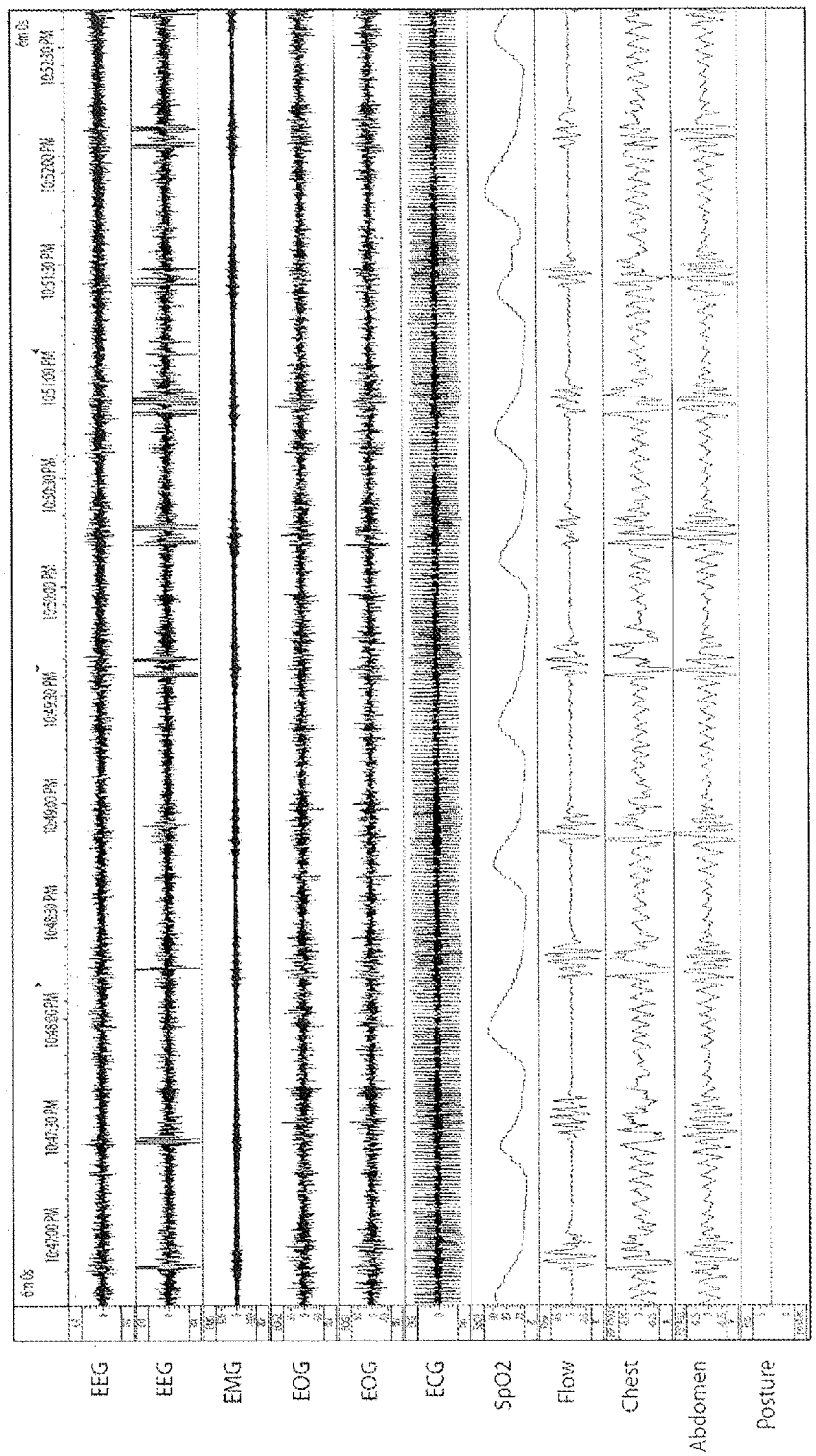

FIG. 6c shows polysomnography of a patient before a treatment. There are eleven signal channels from top to bottom with a 6 minute horizontal span. The top two channels both are EEG (electoencephalogram) from different scalp locations. Periodic spikes in second represent cortical arousal and related activity. The third channel down is submental EMG (electromyogram). Increasing activity around time of arousals represent genioglossus recruitment. The fourth & fifth channels are EOG (electro-oculogram). The sixth channel is an electocardiogram. The seventh channel shows pulse oximetry (SpO2) with repetitive desaturations to below 70% from about 90%. The eighth channel is respiratory airflow using nasal cannula connected to differential pressure transducer. Repetitive apneas of 25 to 35 seconds alternating with 10 to 15 second bursts of recovery breathing coinciding with EEG arousal and increased EMG activity. The ninth shows movement of chest and tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 6D:
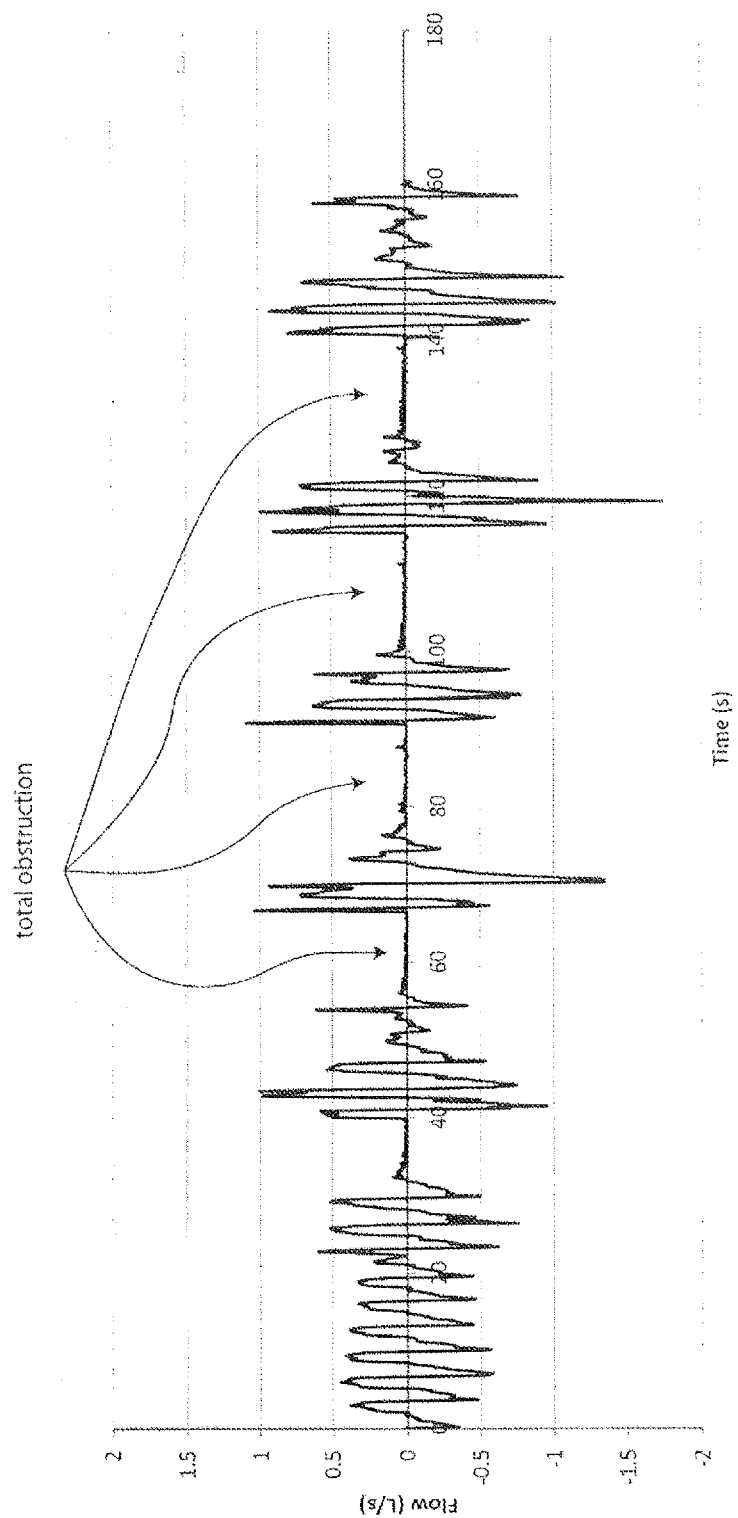

FIG. 6d shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

Figure 6E:
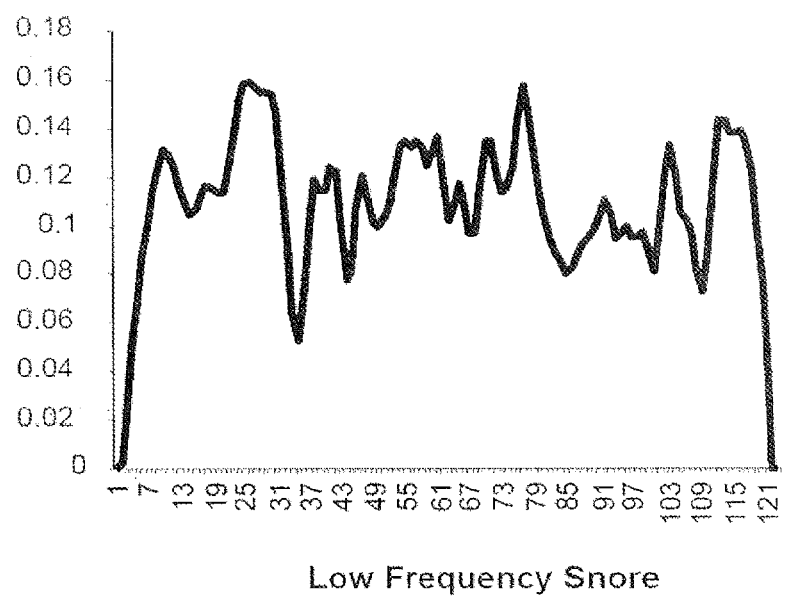

FIG. 6e shows a scaled inspiratory portion of a breath where the patient is experiencing low frequency inspiratory snore.

Figure 6F:
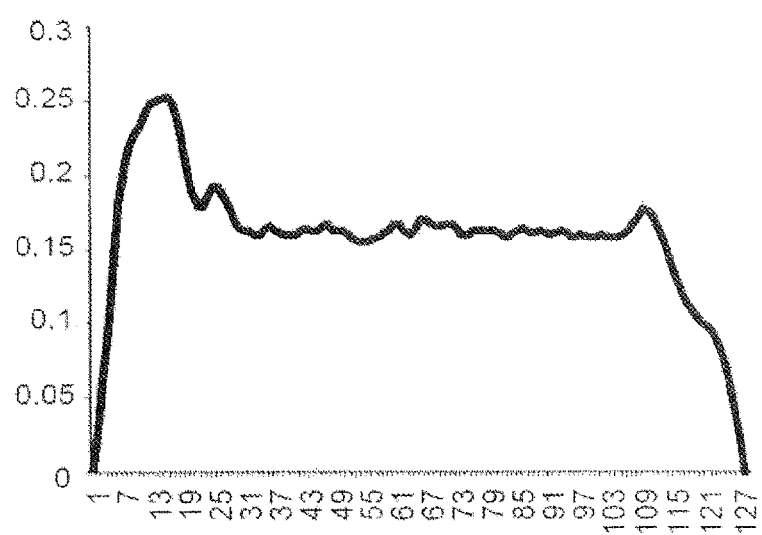

FIG. 6f shows a scaled inspiratory portion of a breath where the patient is experiencing an example of flattened inspiratory flow limitation.

Figure 6G:
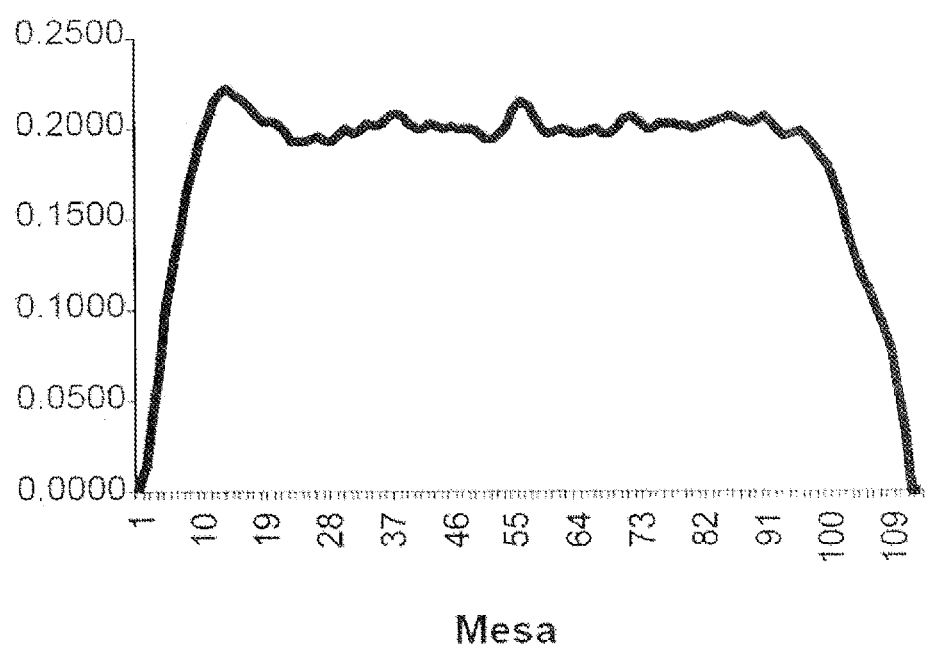

FIG. 6g shows a scaled inspiratory portion of a breath where the patient is experiencing an example of "mesa" flattened inspiratory flow limitation.

Figure 6H:
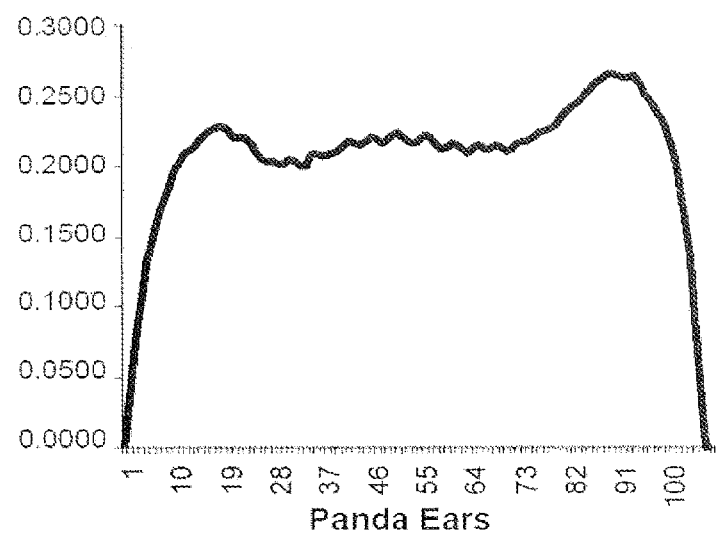

FIG. 6h shows a scaled inspiratory portion of a breath where the patient is experiencing an example of "panda ears" inspiratory flow limitation.

Figure 6I:
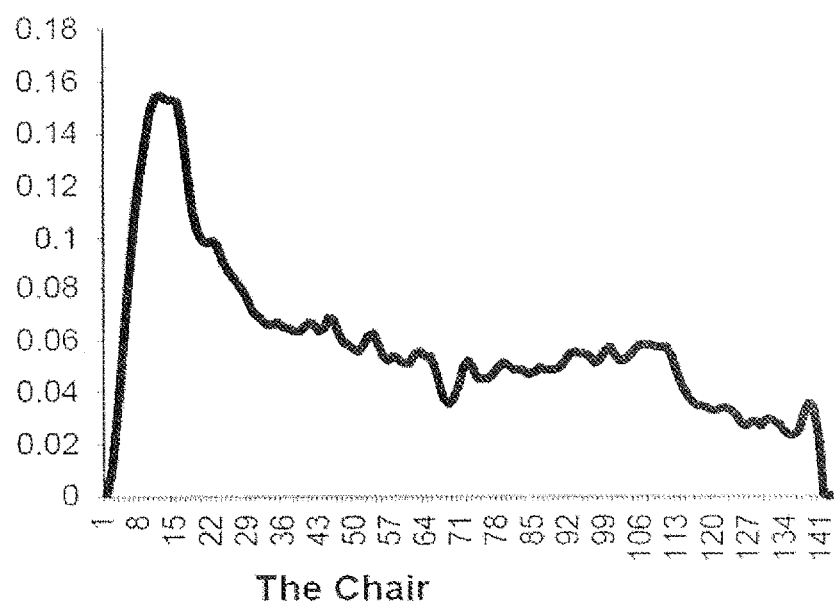

FIG. 6i shows a scaled inspiratory portion of a breath where the patient is experiencing an example of "chair" inspiratory flow limitation.

Figure 6J:
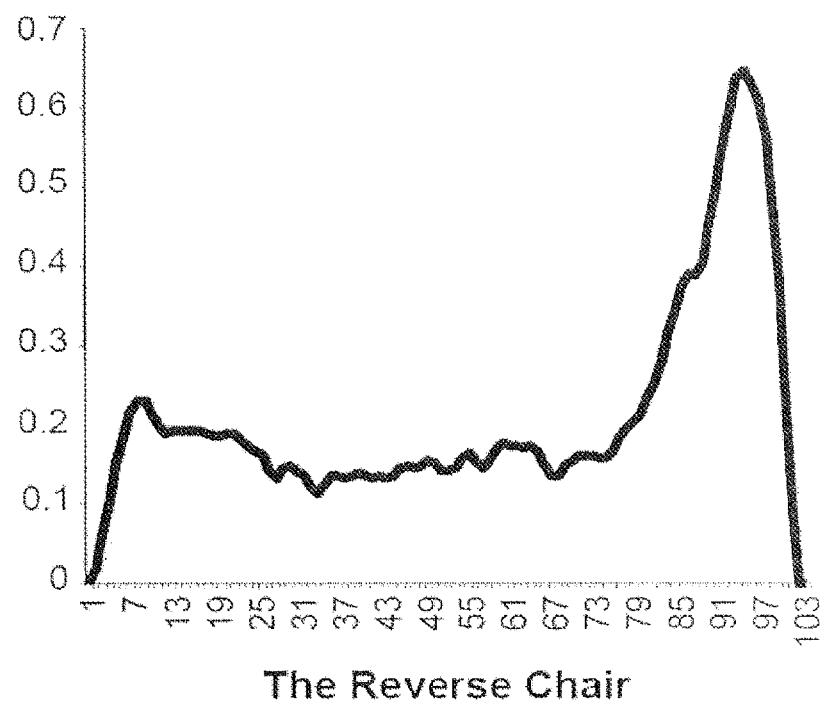

FIG. 6j shows a scaled inspiratory portion of a breath where the patient is experiencing an example of "reverse chair" inspiratory flow limitation.

Figure 6K:
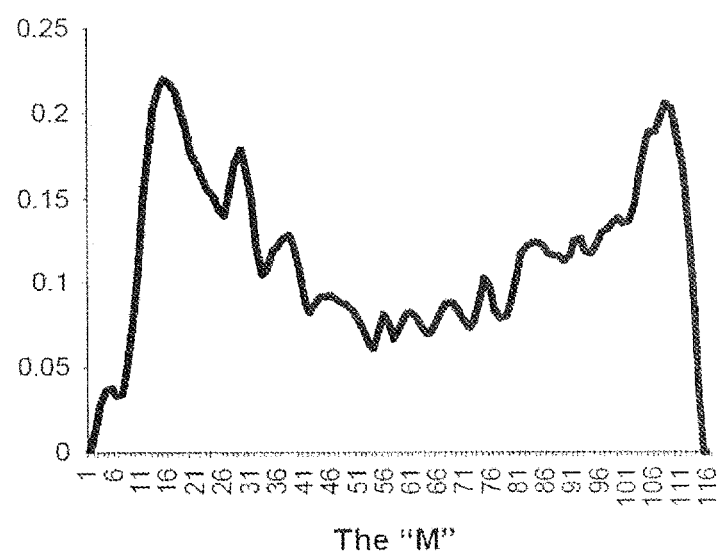
Figure 6I:
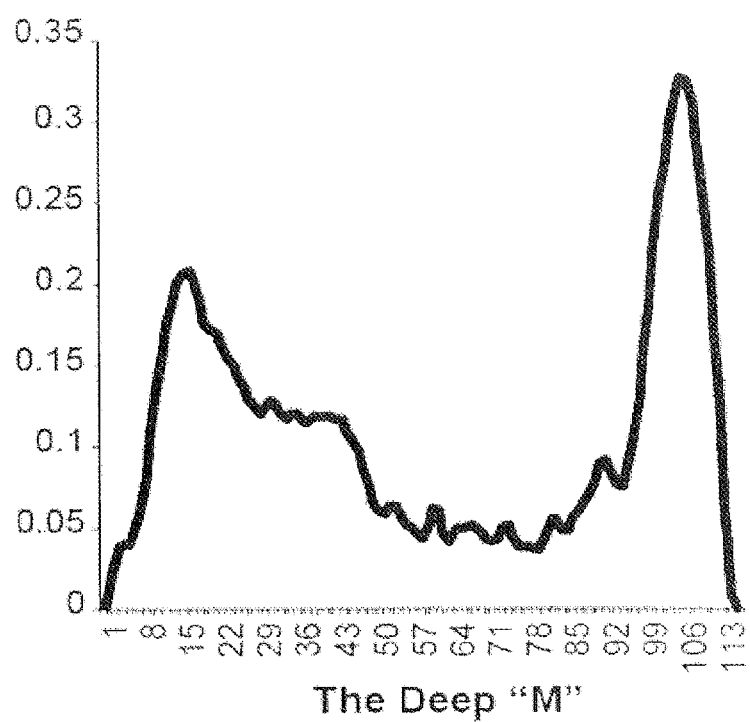

FIG. 6k shows a scaled inspiratory portion of a breath where the patient is experiencing an example of "M-shaped" inspiratory flow limitation.

FIG. 6l shows a scaled inspiratory portion of a breath where the patient is experiencing an example of severely "M-shaped" inspiratory flow limitation.

Figure 6M:
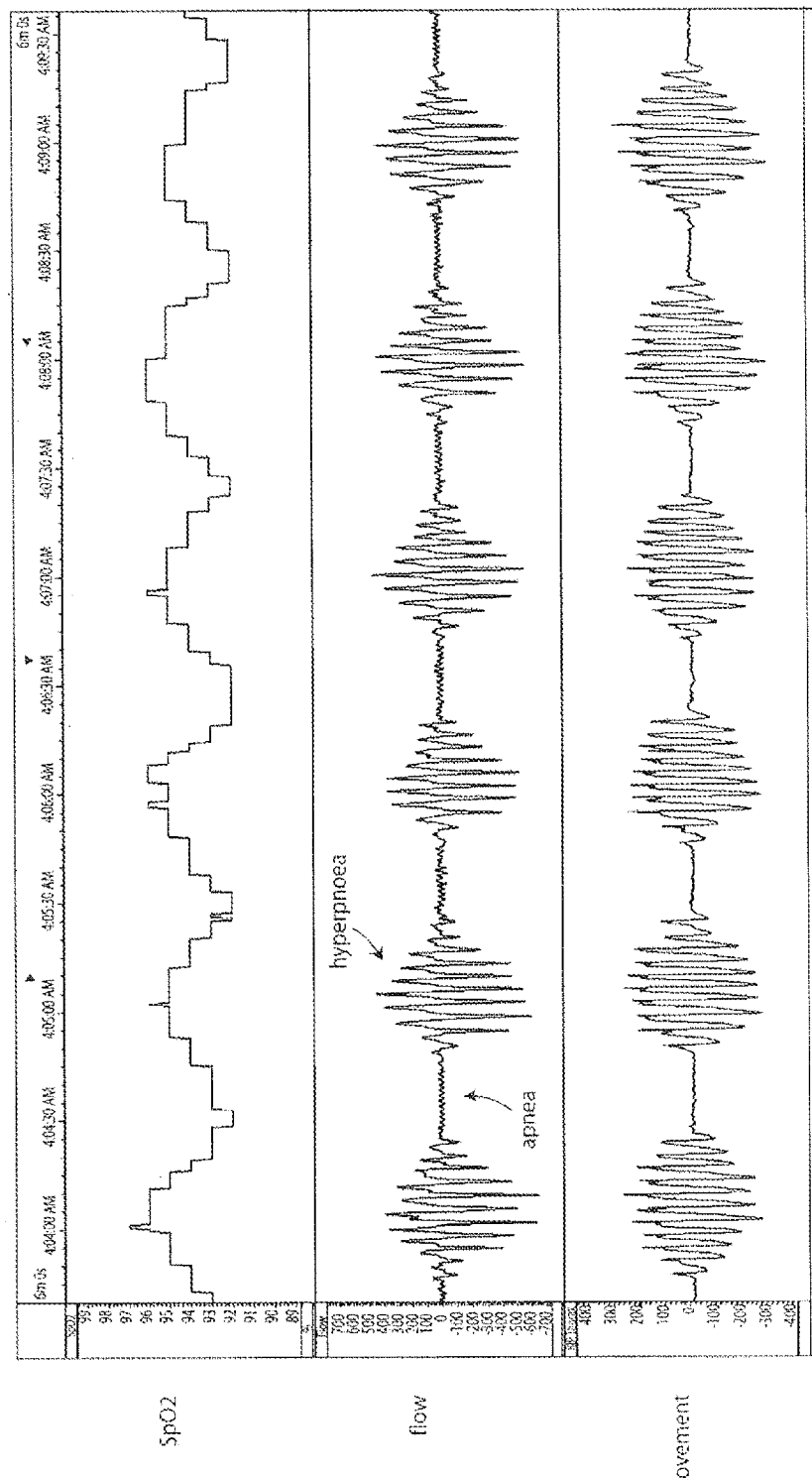

FIG. 6m shows data for a patient with Cheyne-Stokes respiration. There are three channels—oxygen saturation (SpO2), a signal indicative of flow and the third, movement.

The data span six minutes. The signal representative of flow was measured using a pressure sensor connected to nasal cannulae. The patient exhibits apneas of about 22 seconds and hyperpneas of about 38 seconds. Higher frequency low amplitude oscillation during apnea is cardiogenic.

Figure 6N:
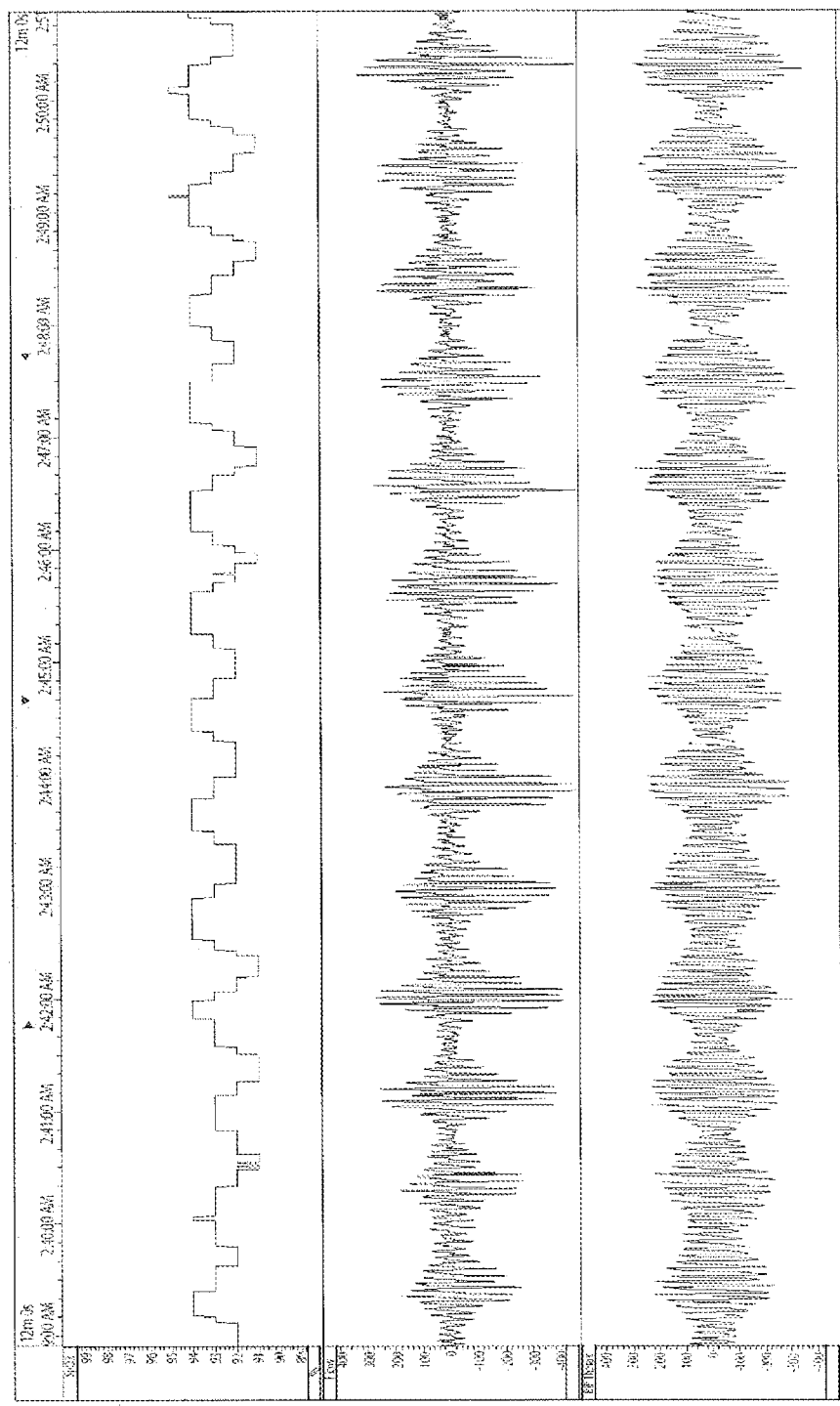

FIG. 6n shows data for a patient with another example of Cheyne-Stokes respiration, using the same three channels as in FIG. 6m. The data span ten minutes. Generally, in the flow data signal of FIG. 6n the patient is experiencing hypopneas in place of the apneas illustrated in FIG. 6m.

4.7 Monitoring Systems

Figure 7:
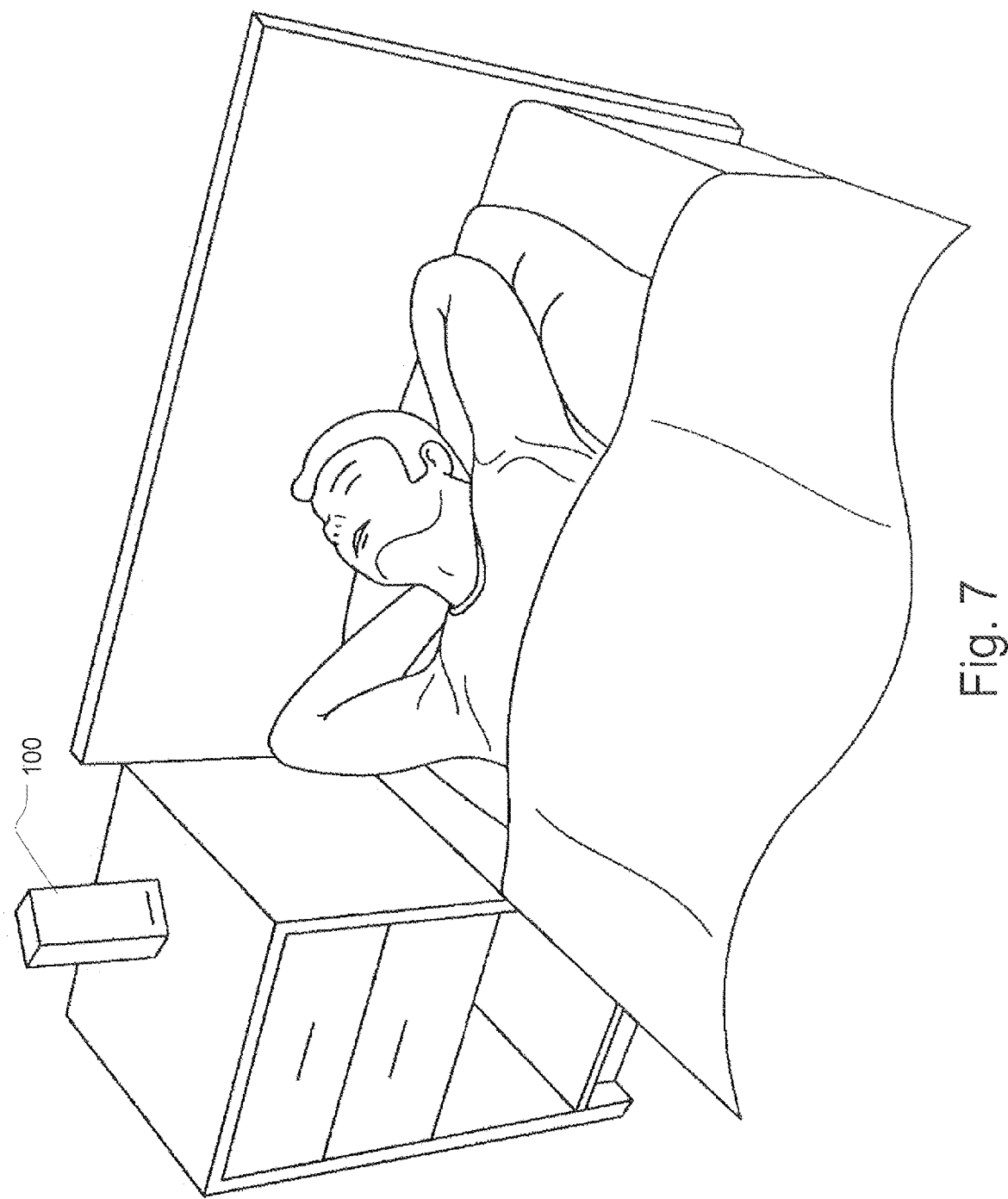

FIG. 7 shows an example non-contact apparatus for monitoring the respiration and/or movement of a patient. It also illustrates how a system of an embodiment might be used in assessment of sleep stage, wherein the system is placed at a bedside table and acquires measurements relating to the movement and breathing of the subject.

4.8 Sleep Stage Processing

Figure 8:
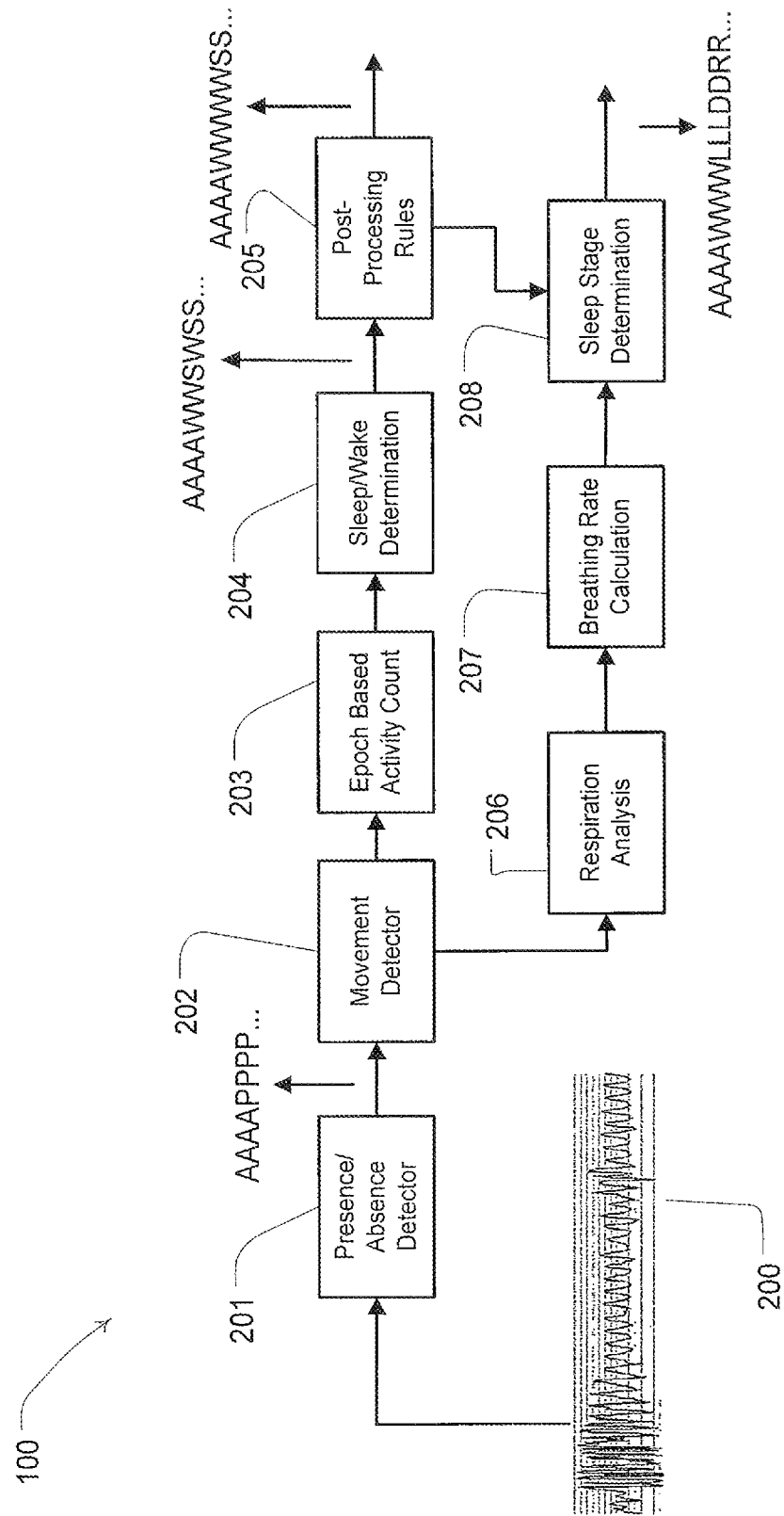

FIG. 8 is a schematic representation of the overall processing of the movement and respiratory signals, in which various levels of outputs are possible, namely, an indicator of whether a subject is present or absent, an indication of whether a person is asleep or awake, or an indication of the sleep stage.

Figure 9:
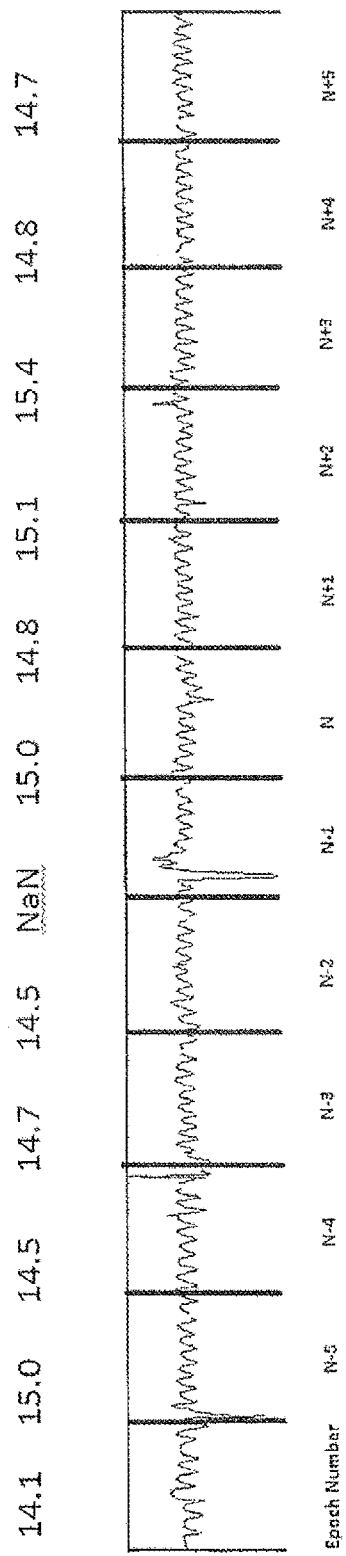

FIG. 9 illustrates a sensor signal divided into epochs, with each epoch associated with a respiration rate.

Figure 10:
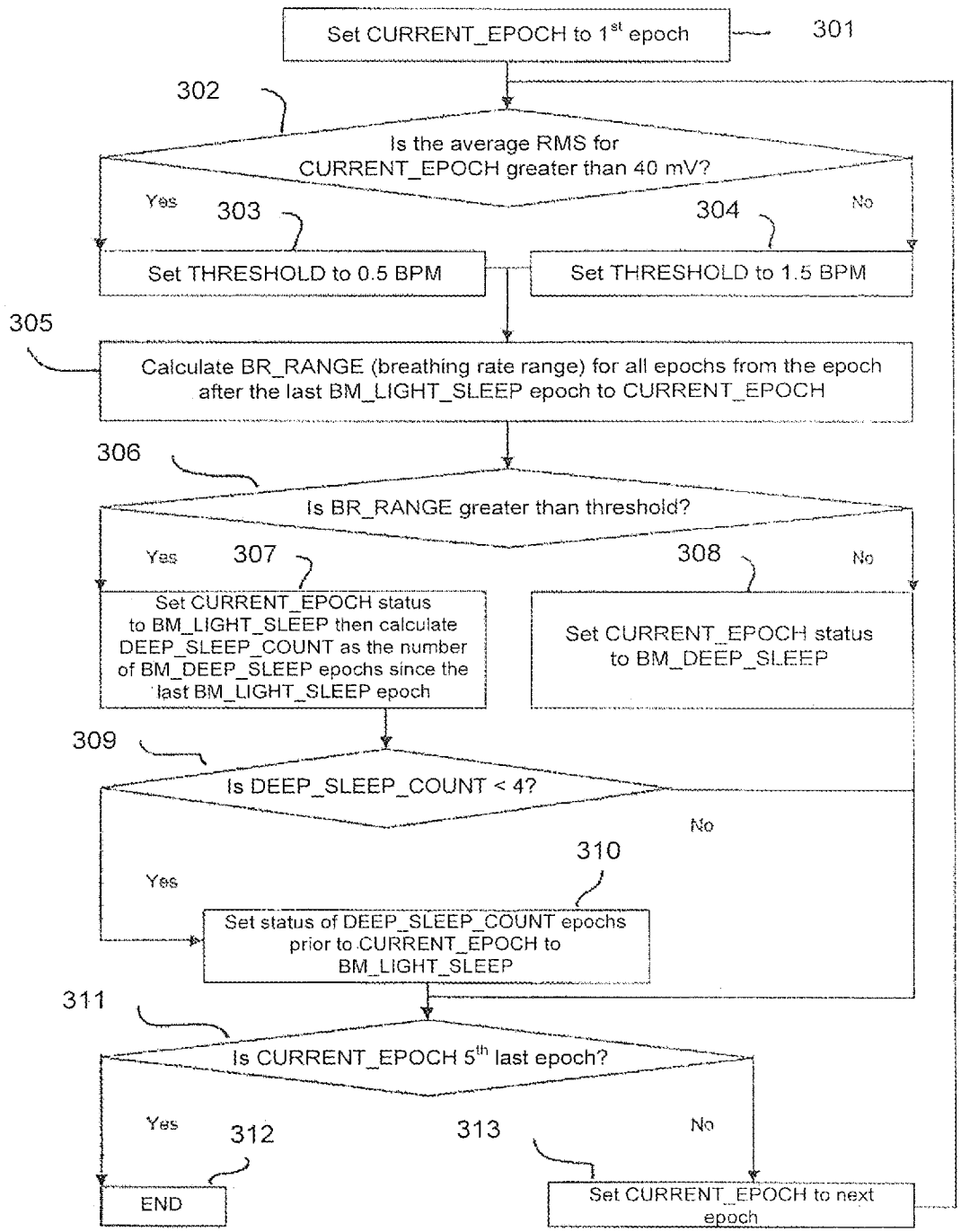

FIG. 10 is a flow diagram of the processing that may be implemented to determine whether a person is in deep sleep (Stage N3 described previously).

Figure 11:
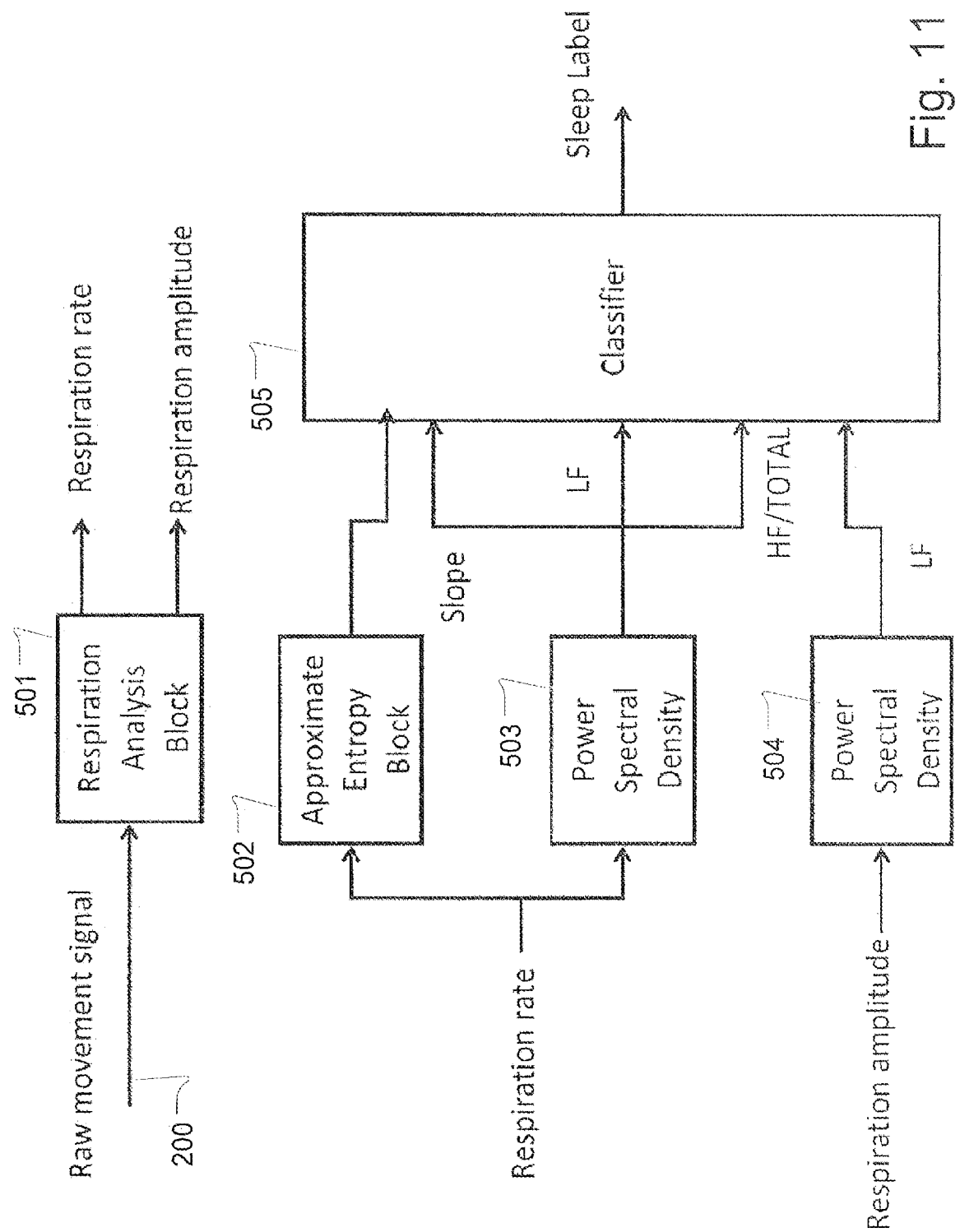

FIG. 11 shows example processes for the classification of a period of sleep on the basis of the variation of the respiration rate and amplitude signals during the period.

Figure 12:
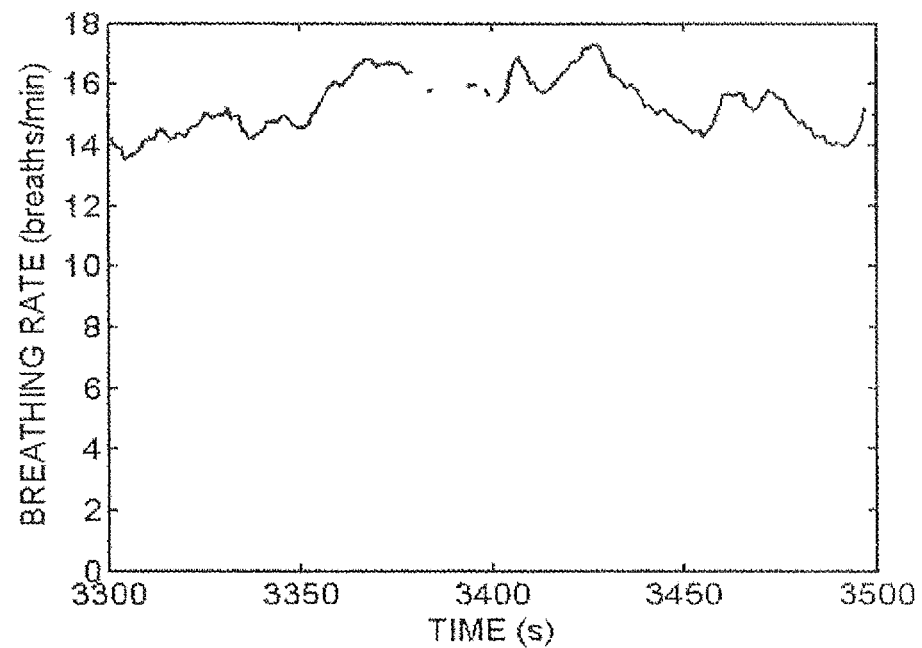
Figure 12:
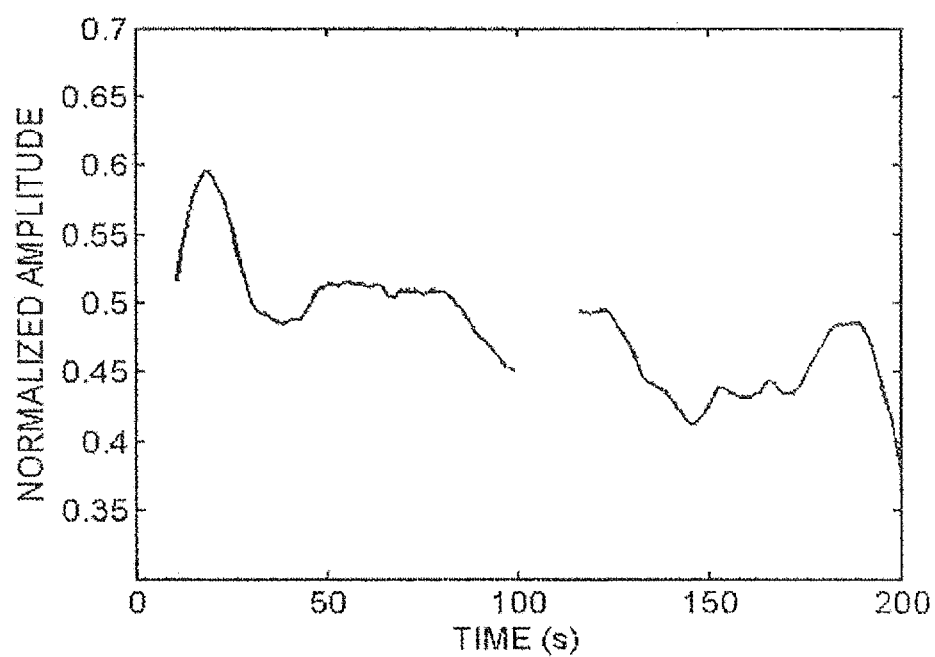

FIG. 12 shows an example of (a) a respiration rate signal and (b) a normalized respiration amplitude signal as a function of time.

Figure 13:
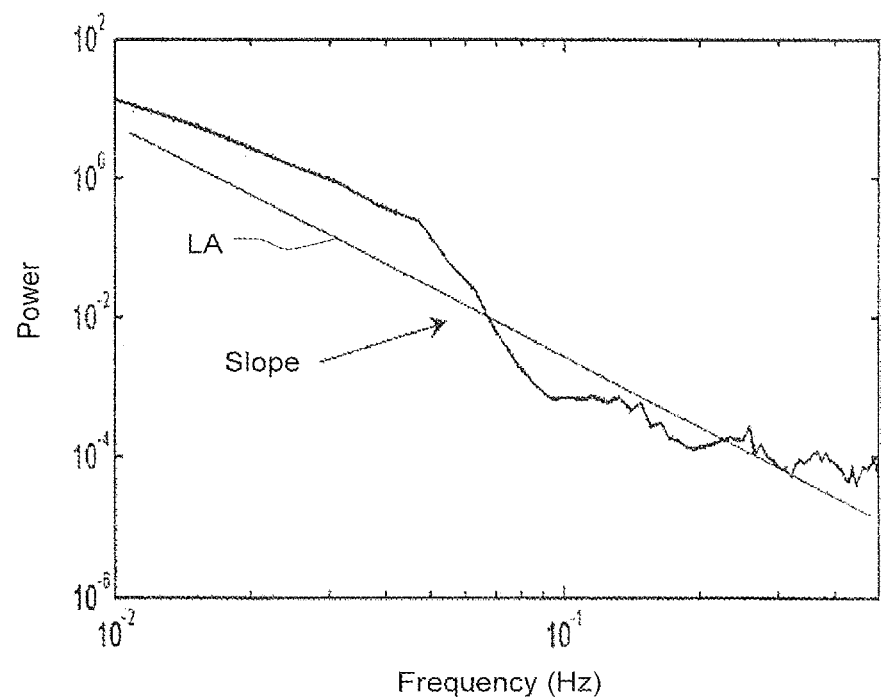
Figure 13:
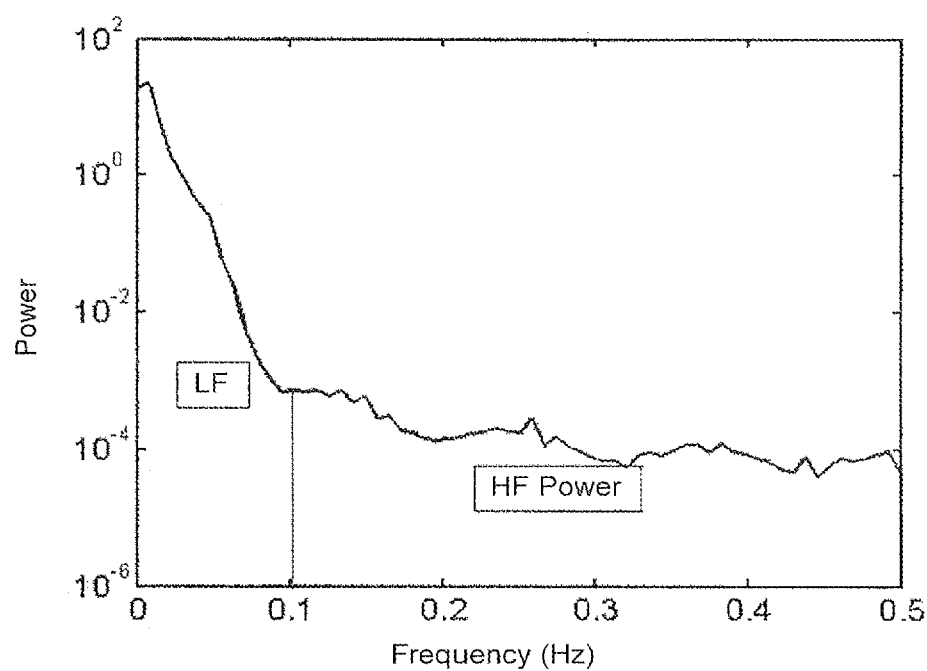

FIG. 13 illustrates an analysis of the power spectral density (PSD) estimate of the respiration rate signal, in which the top graph of FIG. 13 shows a linear fit to the log-log plot of the PSD, and bottom graph shows the power contained within various spectral bands.

Figure 14:
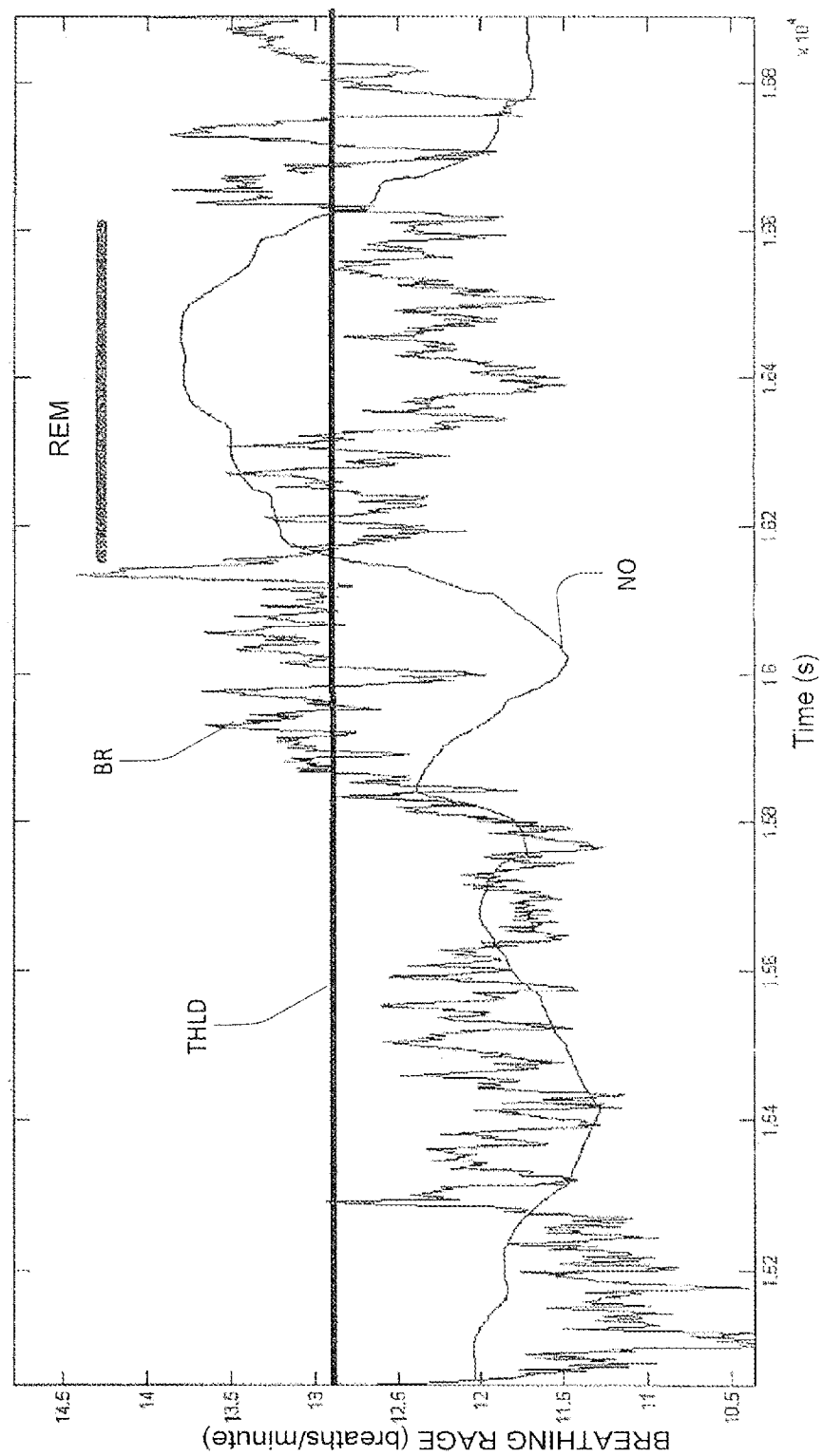

FIG. 14 shows a plot of the respiration rate over a period of time, the internal discriminant value of the classifier, and the final output of the sleep stage classifier shown in FIG. 11, thus illustrating how an output indication of a sleep stage (REM Sleep) can be derived from respiration signals.

Figure 15:
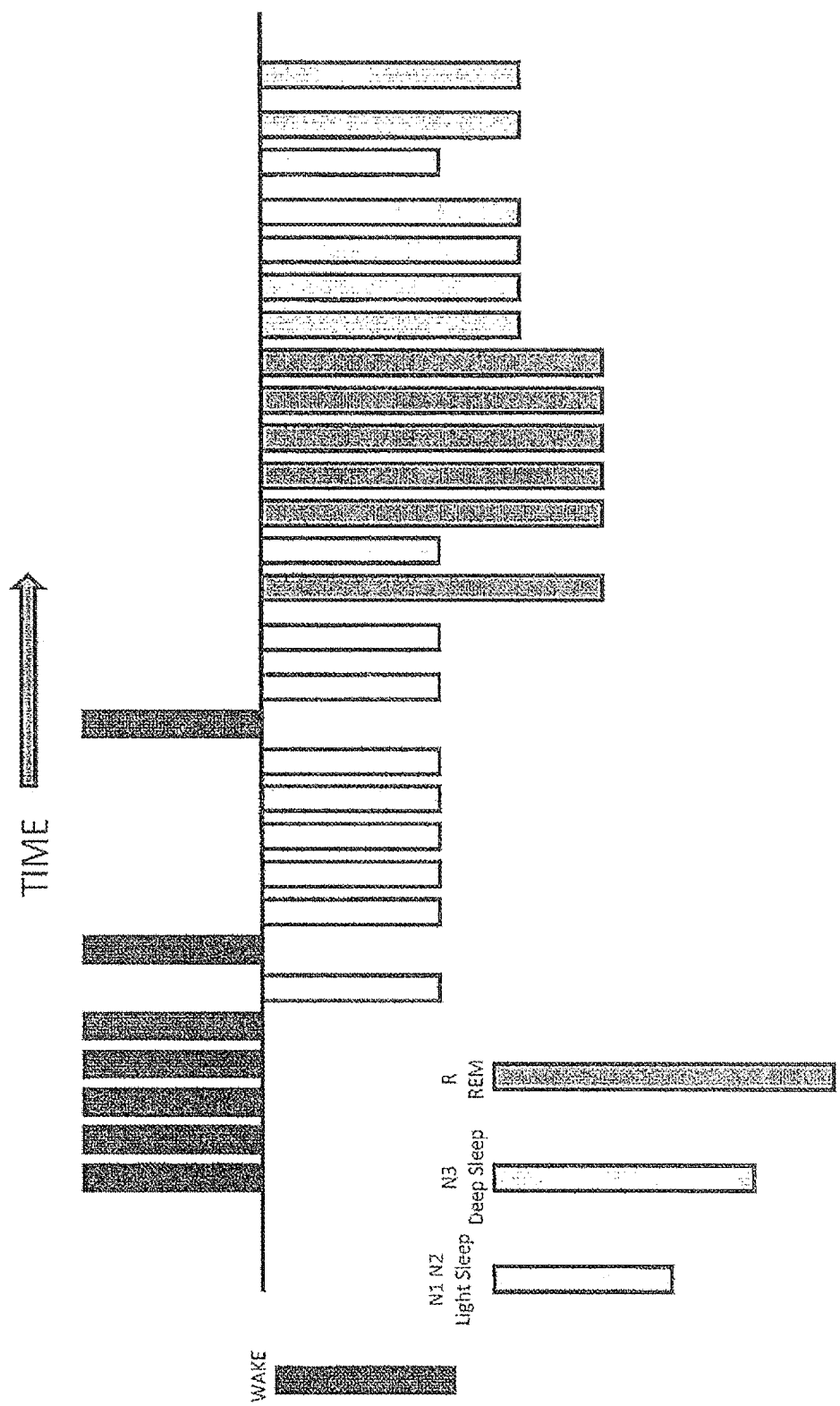

FIG. 15 is an output diagram showing how the system assigns data (e.g., sleep stage indications) chronologically to epochs.

Figure 16:
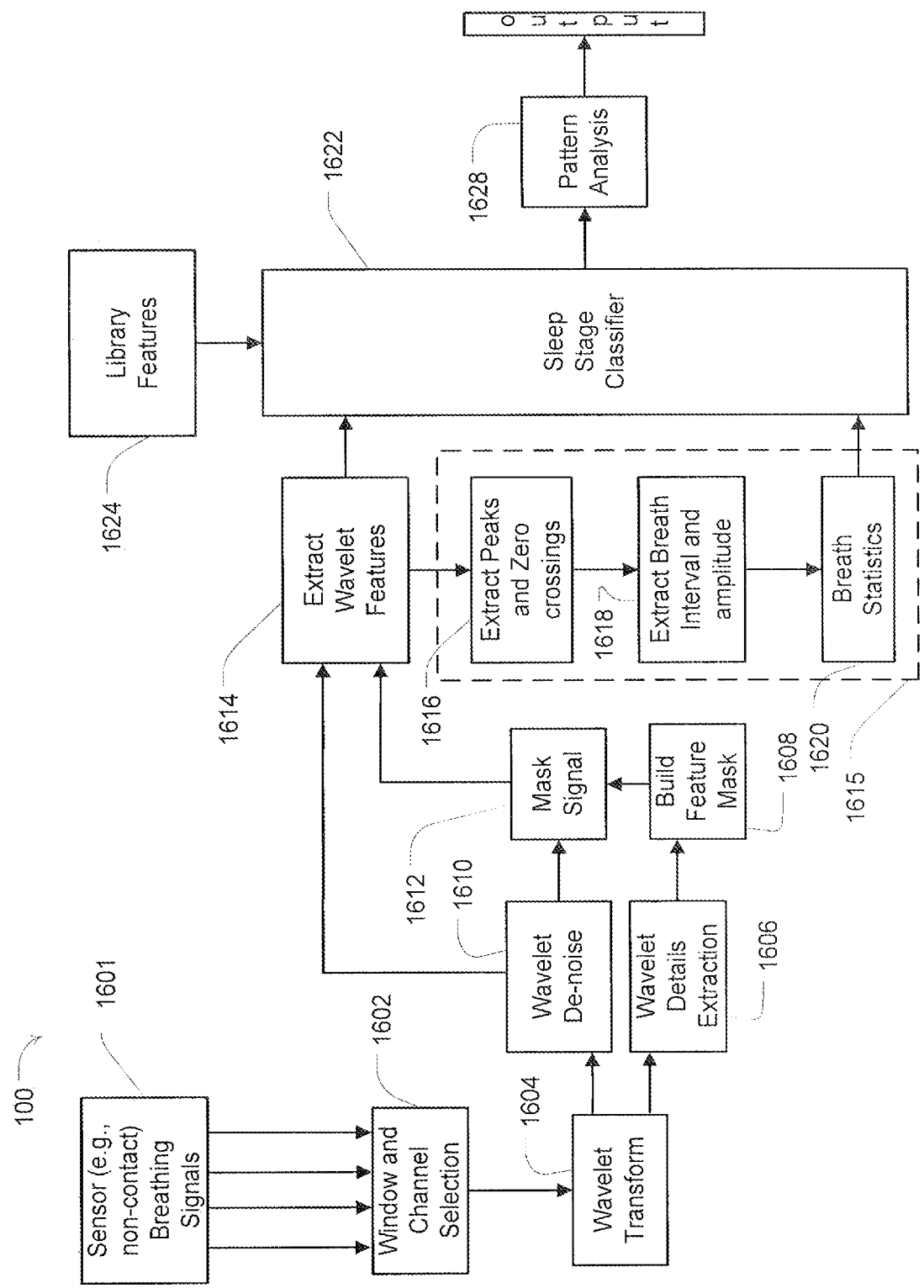

FIG. 16 is a processing diagram illustrating example processes or processing components that may be involved in a sleep stage detector suitable for implementation in some embodiments of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Treatment Systems

In one form, the present sleep stage monitor technology may be incorporated within or in communication (wired or wireless) with apparatus for treating a respiratory disorder. The apparatus may comprise a flow generator or blower for supplying pressurised respiratory gas, such as air, to the patient 1000 via an air delivery tube leading to a patient interface 3000.

5.2 Therapy

In one form, the present technology comprises a method for treating a respiratory disorder comprising the step of applying or adjusting positive pressure to the entrance of the airways of a patient 1000, such as in response to or based upon a particular detection of sleep stage made by the sleep stage monitor. The treatment (e.g. positive pressure) may be any type such as a CPAP treatment, automatic titrating pressure (APAP), bi-level PAP or other suitable respiratory treatment.

5.2.1 Nasal CPAP for OSA

For example, in one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

In certain embodiments of the present technology, mouth breathing is limited, restricted or prevented.

5.3 Patient Interface 3000

A non-invasive patient interface 3000 in accordance with one aspect of the present technology may optionally include any one or more of the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120. Preferably the sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber 3200

Preferably the plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

5.3.3 Positioning and Stabilising Structure 3300

Preferably the seal-forming portion of the patient interface 3000 of the present technology is held in sealing position in use by the positioning and stabilising structure 3300.

5.3.4 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel 3510.

5.3.5 Decoupling Structure(s) 3500

In one form the patient interface 3000 includes at least one decoupling structure 3500, for example a swivel 3510 or a ball and socket 3520.

5.3.6 Connection Port 3600

Connection port 3600 allows for connection to the air circuit 4170.

5.3.7 Forehead Support 3700

In one form, the patient interface 3000 includes a forehead support 3700.

5.3.8 Anti-Asphyxia Valve 3800

In one form, the patient interface 3000 includes an anti-asphyxia valve 3800.

5.3.9 Ports 3900

In one form of the present technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

5.4 PAP Device 4000

An example PAP device 4000 in accordance with one aspect of the present technology may be formed with mechanical and pneumatic components 4100, electrical components 4200 and may be programmed to execute one or more algorithms 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124. One or more pressure sensors and flow sensors are included in the pneumatic path.

The preferred pneumatic block 4020 comprises a portion of the pneumatic path that is located within the external housing 4010.

The PAP device 4000 preferably has an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute one or more algorithm modules 4300, preferably including a pre-processing module 4310, a therapy engine module 4320, a pressure control module 4330, and further preferably a fault condition module 4340.

5.4.1 PAP Device Mechanical & Pneumatic Components 4100

5.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

5.4.1.2 Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

5.4.1.3 Pressure Device 4140

In an example form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 may be under the control of the therapy device controller 4240.

5.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

5.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit 4170

An air circuit 4170 in accordance with an aspect of the present technology is constructed and arranged to allow a flow of air or breathable gasses between the pneumatic block 4020 and the patient interface 3000.

5.4.1.7 Oxygen Delivery

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

5.4.2 PAP Device Electrical Components 4200

5.4.2.1 Basic PAP Device

Some basic PAP devices, such as PAP device 4000, are essentially electromechanical devices that do not include processing capabilities.

5.4.2.1.1 Power Supply 4210

Power supply 4210 supplies power to the other components of the basic PAP device 4000: the input device 4220, the central controller 4230, the therapy device 4245, and the output device 4290.

In one form of the present technology, power supply 4210 is internal of the external housing 4010 of the PAP device 4000. In another form of the present technology, power supply 4210 is external of the external housing 4010 of the PAP device 4000.

5.4.2.1.2 Input Device(s) 4220

Input devices 4220 comprises buttons, switches or dials to allow a person to interact with the PAP device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.1.3 Central Controller 4230

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

5.4.2.1.4 Therapy Device 4245

In one form of the present technology, the therapy device 4245 is configured to deliver therapy to a patient 1000 under the control of the central controller 4230. Preferably the therapy device 4245 is a positive air pressure device 4140.

5.4.2.1.5 Output Device 4290

An output device 4290 in accordance with the present technology may take the form of one or more of a visual, audio, and haptic output. A visual output may be a Liquid Crystal Display (LCD) or Light Emitting Diode (LED) display. An audio output may be a speaker or audio tone emitter.

5.4.2.2 Microprocessor-Controlled PAP Device

5.4.2.2.1 Power Supply 4210

In one form of the present technology power supply 4210 is internal of the external housing 4010 of the PAP device 4000. In another form of the present technology, power supply 4210 is external of them.

In one form of the present technology power supply 4210 provides electrical power to the PAP device 4000 only. In another form of the present technology, power supply 4210 provides electrical power to both PAP device 4000 and humidifier 5000.

5.4.2.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.2.3 Central Controller 4230

In one form of the present technology, the central controller 4230 is a processor suitable to control a PAP device 4000 such as an x86 INTEL processor.

A processor suitable to control a PAP device 4000 in accordance with another form of the present technology includes a processor based on ARM Cortex-M processor from ARM Holdings. For example, an STM32 series microcontroller from ST MICROELECTRONICS may be used.

Another processor suitable to control a PAP device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor for the PAP device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

The processor, or multiple such processors, is configured to implement the one or more methodologies described herein such as the one or more algorithms 4300 expressed as computer programs stored in a computer readable storage medium, such as memory 4260. In some cases, as previously discussed, such processor(s) may be integrated with a PAP device 4000. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

5.4.2.2.4 Clock 4232

Preferably PAP device 4000 includes a clock 4232 that is connected to processor.

5.4.2.2.5 Therapy Device Controller 4240

In one form of the present technology, therapy device controller 4240 is a pressure control module 4330 that forms part of the algorithms 4300 executed by the processor.

In one form of the present technology, therapy device controller 4240 is a dedicated motor control integrated circuit. For example, in one form a MC33035 brushless DC motor controller, manufactured by ONSEMI is used.

5.4.2.2.6 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

5.4.2.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

In one form of the present technology, the memory 4260 acts as a computer readable storage medium on which is stored computer program instructions expressing the one or more methodologies described herein, such as the one or more algorithms 4300.

5.4.2.2.8 Transducers 4270

Transducers may be internal of the device, or external of the PAP device. External transducers may be located for example on or form part of the air delivery circuit, e.g. the patient interface. External transducers may be in the form of non-contact sensors such as a Doppler radar movement sensor that transmit or transfer data to the PAP device.

5.4.2.2.8.1 Flow

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element. Other flow sensors may be implemented such as a hot wire mass airflow sensor.

In use, a signal representing total flow Qt from the flow transducer 4274 is received by the processor.

5.4.2.2.8.2 Pressure 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor. In one form, the signal from the pressure transducer 4272 is filtered prior to being received by the processor.

5.4.2.2.8.3 Motor Speed 4276

In one form of the present technology a motor speed signal 4276 is generated. A motor speed signal 4276 is preferably provided by therapy device controller 4240. Motor speed may, for example, be generated by a speed sensor, such as a Hall effect sensor.

5.4.2.2.9 Data Communication Systems

In one preferred form of the present technology, a data communication interface 4280 is provided, and is connected to processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor. In another form, data communication interface 4280 is an integrated circuit that is separate from processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

5.4.2.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.2.10.1 Display Driver 4292

A display driver 4292 receives as an input the characters, symbols, or images intended for display on the display 4294, and converts them to commands that cause the display 4294 to display those characters, symbols, or images.

5.4.2.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 PAP Device Algorithms 4300

5.4.3.1 Pre-Processing Module 4310

An pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation algorithm 4312, vent flow algorithm 4314, leak flow algorithm 4316, respiratory flow algorithm 4318, and jamming detection 4319.

5.4.3.1.1 Pressure Compensation 4312

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

5.4.3.1.2 Vent Flow

In one form of the present technology, a vent flow calculation algorithm 4314 receives as an input an estimated pressure, Pm, in the patient interface 3000 and estimates a vent flow of air, Qv, from a vent 3400 in a patient interface 3000.

5.4.3.1.3 Leak Flow

In one form of the present technology, a leak flow algorithm 4316 receives as an input a total flow, Qt, and a vent flow Qv, and provides as an output a leak flow Ql by calculating an average of Qt−Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt−Qv, and low pass filtered square root of pressure Pm, where the low pass filter time constant has a value sufficiently long to include several breathing cycles, e.g. about 10 seconds.

5.4.3.1.4 Respiratory Flow

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

5.4.3.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output, one or more therapy parameters in a therapy parameter determination process 4329.

In one form of the present technology, a therapy parameter is a CPAP treatment pressure Pt.

In one form of the present technology, a therapy parameter is one or more of a level of pressure support, and a target ventilation.

5.4.3.2.1 Phase Determination

In one form of the present technology, the PAP device 4000 does not determine phase.

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation.

In one form, the phase output is a discrete variable with values of one of inhalation, mid-inspiratory pause, and exhalation.

In one form, the phase output is a continuous variable, for example varying from 0 to 1, or 0 to 2Pi.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

5.4.3.2.2 Waveform Determination 4322

In one form of the present technology, a control module 4330 controls a therapy device 4245 to provide an approximately constant positive airway pressure throughout a respiratory cycle of a patient.

In one form of the present technology, a control module 4330 controls a therapy device 4245 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure vs. phase.

5.4.3.2.3 Ventilation Determination

In one form of the present technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as the half the low-pass filtered absolute value of respiratory flow, Qr.

5.4.3.2.4 Determination of Inspiratory Flow Limitation

In one form of the present technology, a processor executes one or more algorithms for the detection of inspiratory flow limitation.

In one form the inspiratory flow limitation algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor for the preceding several inspiratory events. This is repeated over the same inspiratory events for the second such point, and so on. Thus, for example, sixty five scaled data points are generated by a processor, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

5.4.3.2.5 Determination of Apneas and Hypopneas 4325

In one form of the present technology, a processor executes one or more algorithms for the determination of the presence of apneas and/or hypopneas.

Preferably the one or more algorithms receive as an input a respiratory flow signal Qr and provide as an output a flag that indicates that an apnea or respectively an hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

5.4.3.2.6 Determination of Snore

In one form of the present technology, a processor executes one or more snore algorithms for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

5.4.3.2.7 Determination of Airway Patency

In one form of the present technology, a processor executes one or more algorithms for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow signal Qr, and determines the presence or absence of a cardiogenic signal. The absence of a cardiogenic signal is taken to be an indication of a closed airway.

5.4.3.2.8 Determination of Treatment Pressure

In one form of the present technology, processor executes one or more algorithms for the determination of a target treatment pressure Pt.

For example, the therapy parameter determination process 4329 receives input such as one of more of the following:
 i. A measure of respiratory phase;
 ii. A waveform;
 iii. A measure of ventilation;
 iv. A measure of inspiratory flow limitation;
 v. A measure of the presence of apnea and/or hypopnea;
 vi. A measure of the presence of snore;
 vii. a sleep stage indication; and
 viii. A measure of the patency of the airway.

This processing may determine the treatment pressure Pt as a function of indices or measures of one or more of flow limitation, apnea, hypopnea, patency, sleep stage and snore and also may optionally rely on a target ventilation from a target ventilation determination process 4328. In one implementation, these measures are determined on a single breath basis, rather than on an aggregation of several previous breaths.

5.4.3.3 Control Module 4330

A control module 4330 in accordance with one aspect of the present technology receives as an input a target treatment pressure Pt, and controls a therapy device 4245 to deliver that pressure.

A control module 4330 in accordance with one aspect of the present technology receives as an input an EPAP pressure and an IPAP pressure, and controls a therapy device 4245 to deliver those respective pressures.

5.4.3.4 Detection of Fault Conditions 4340

In one form of the present technology, a processor executes one or more methods for the detection of fault conditions. Preferably the fault conditions detected by the one or more methods includes at least one of the following:
 Power failure (no power, or insufficient power)
 Transducer fault detection
 Failure to detect the presence of a component Operating parameters outside recommended ranges (e.g. pressure, flow, temperature, $PaO_2$)

Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm

Sending a message to an external device

Logging of the incident

5.4.3.5 Therapy Device 4245

In a preferred form of the present technology, the therapy device 4245 is under the control of the control module 4330 to deliver therapy to a patient 1000.

Preferably the therapy device 4245 is a positive air pressure device 4140.

5.5 Humidifer 5000

5.5.1 Humidifier

In one form of the present technology there is provided a humidifier 5000 which may typically include a water reservoir and a heating plate.

5.6 Sleep Stage Monitors

FIG. 7 is a diagram illustrating an example monitoring embodiment. The sensor, processing and display means may be embodied in one unit, shown as monitoring apparatus 100. In some cases, the sensing modality may be totally non-contact, and may operate through the means of transmitting electromagnetic waves towards the subject. The device may be configured to be sensitive to movement within a distance of 1.2 m, and avoid detecting movement from more distant objects. This ensures that interference from a second person in the bed or nearby moving objects such as fans is minimised. Thus, the sensor may be processed to further derive respiration signals. However, it will be understood that in some versions of the present technology others sensors, such as those further described herein, may also or alternatively be employed to generate movement and/or respiration signals for the detection of sleep stage.

In one non-contact sensing embodiment the radiation used is in the microwave range, in which the sensor is of the type described in U.S. Pat. No. 6,426,716, the entire contents of which are incorporated herein by reference.

In another embodiment, the radiation is in the form of narrow virtual transmit pulses synthesized by differencing long-duration staggered pulse repetition interval (PM) transmit pulses. Such a sensor is described in U.S. Pat. No. 7,952,515, the entire contents of which are incorporated herein by reference.

In the cases where these radio-frequency based sensors are used, they will produce so-called quadrature signals I and Q which represent the detected movement observed from positions 90° apart in the phase space of the transmitter. An advantage of this approach is that it can help determine the direction of movement, and also smooth out the overall sensitivity of the system.

In general, embodiments of the present technology may include a sleep monitoring device or apparatus that may have one or more processors or utilize a processor of another apparatus, such as any of the processors described throughout this specification, to implement particular sleep stage detection methodologies such as with the algorithms/processes described in more detail herein. Thus, the device or apparatus may include integrated chips, a memory and/or other control instruction, data or information storage medium. For example, programmed instructions encompassing such detection methodologies may be coded on integrated chips in the memory of the device or apparatus to form one or more application specific integrated chips (ASIC). Such instructions may also or alternatively be loaded as software or firmware using an appropriate data storage medium. Thus, the processes may be embodied in processor control instructions and data for controlling apparatus to perform the methodologies and may be contained in any appropriate computer or machine readable recording medium of the non-transitory type such as in the form of software for use by a general purpose computer so that the general purpose computer may serve as a specific purpose computer according to any of the methodologies discussed herein upon loading the software into the general purpose computer.

FIG. 8 shows an example of a process and/or processing means (e.g., one or more processors and/or processing circuits) implemented by the system to generate indicators of sleep stages. The sensor acquires at least one signal 200 which represents the movement of the body. In general, this movement will include components due to breathing effort or cardiac activity, as well as other movements not related to respiratory or cardiac functions. Examples of such general body movements, which throughout this description are referred to as "bodily movement", include turning over, twitching, adjusting position etc. Signals indicative of these movements could be provided by a radio frequency bio-motion sensor, but could also be acquired by one or more respiratory inductance plethysmography, flow sensors, by pressure sensors embedded in a sensor film or sensor mattress, by a bioimpedance measurement system, by an end-tidal $CO_2$ respiratory monitor, by an ultrasonic sensor, or by an optical sensor.

An initial step of processing may be to determine whether a person is present or absent using the presence-absence detector 201. The means for determining presence or absence can be through measurement of the amplitude of the signal (e.g., the root mean square (RMS) value of the signal) or could involve more complex processing such as determining the spectral content of the signal relative to the expected noise floor of the sensor(s). In one embodiment the processing is performed in a manner as described in International Patent Cooperation Treaty Publication No. WO2007/143535, the entire contents of which are incorporated herein by reference. In another embodiment, periods of movement can be determined by taking the arctangent of the quadrature I and Q signals mentioned above. In this case, the resulting signal will be related directly to the displacement of the object being observed, if normalization and phase unwrapping is correctly carried out. Given the displacement signal, presence-absence can then be determined by seeing if the energy in the displacement signal is greater than a set threshold.

The output of the presence-absence detector stage of processing may be a sequence of epoch labels such as "AAAAPPP", where "A" represents absent and "P" represents present, and an epoch may represent a fixed period of time such as 30 seconds. The signal is then fed to a movement detector 202 which determines whether any movement is present (typically on a shorter time scale such as 1 second). A means for determining movement may be through counting level-crossings of the signal, or by measuring the high frequency content of the signal. The detailed methodology of such measurement is described in International Patent Cooperation Treaty Publication No. WO2007/143535.

Each second can then be associated with movement or non-movement. The outcomes of each 1-second movement detector can be combined into an epoch-based activity counter 203. For example, if an epoch is 30 seconds, and each 1-second period within an epoch has movement, then the overall activity count for that epoch is 30. The amplitude of the movement detected can also be included in the activity count metric. Based on the activity count, a sleep wake determination means 204 assigns labels based on the level of the activity count (for example, an activity count greater than 20 may be considered as a wake epoch). The activity counts of surrounding epochs may also be considered in making this determination. The post-processing rules assessor 205 can be further used to enhance the accuracy of the sleep/wake determination, by for example, removing single isolated epochs of SLEEP surrounded by WAKE. The overall output of the post-processing rules can be a sequence of labels (which can combine the information from the presence/absence detector) and may look like; "AAAAWWWWWSSSSSS", where "A" represents absent, "W" represents wake, and "S" represents sleep.

In parallel to determining the sleep/wake status, further processing is implemented to determine the sleep stage. The respiration analysis block 206 enhances the respiration signal, for example, by filtering the raw input signal from the movement detector 202 with a low pass filter. Using the information from the movement detector 202, the respiration analysis may also label certain sections of signal as unreliable for respiration rate estimation. For example, if the signal is determined to contain indications of large movements, the signal may be so marked so it may be avoided in respiration rate estimate calculations. The respiration rate calculator 207 is used to determine the breathing rate of the person, for example, in breaths/minute or in Hz. The respiration rate can be calculated with a power spectral density estimate, or with an auto-regressive model of the signal. The detailed methodology of such a calculation is described in International Patent Publication No. WO2007/143535. The calculation provides estimates of the respiration rate, for example, on a per-epoch basis, or alternatively on a shorter time scale (e.g., once/second). These respiration rates are provided to the sleep stage determination means 208 which may use the respiration rates to determine sleep stage. For example, in one embodiment, the respiration rate is used to distinguish deep sleep (Stage N3) from all other stages of sleep (N1, N2 and REM). The relative amplitude of respiration can also be determined and used in the sleep stage determination.

For explanatory purposes, FIG. 9 illustrates an example output of the respiration rate calculation 207 from FIG. 8. In this, it is shown how the signal can be considered in epochs (30 seconds in this case) and how each epoch may have a single respiration rate associated with it. For example, each respiration rate is the rate associated with the maximum power spectral density of the epoch. The epochs may be identified sequentially such as with a suitable label e.g., Epoch N, N+1, etc. In the illustration, Epoch N−5 has a rate of 15 breaths/minute, N−4 has a rate of 14.5 breaths/min, etc. Also, as an illustrative point, the respiration analysis block 206 has determined that Epoch N−1 has a sufficiently large movement so that it cannot supply a reliable respiration rate. In such cases, the epoch rate might be identified suitably such as with a label representing that it is "Unavailable" or "Not a Number" etc.

FIG. 10 shows in more detail a specific embodiment of a processing methodology for sleep stage determination means 208 from FIG. 8. The general principle of operation is to determine a sequence of epochs where the respiration rate is sufficiently stable. The set of SLEEP/WAKE labels for an entire recording is input to the process algorithm. The processing may be initiated by assigning (at 301) the variable "CURRENT EPOCH" to be the first epoch in the series.

The processing then decides at 302 whether the CURRENT EPOCH has a high amplitude signal (representing good signal quality). If the signal quality is good, then the algorithm can be very confident in the estimate of respiration rate. Thus, the signal quality may be evaluated for the setting of a stability threshold to gauge breathing rate variability. In this embodiment, an average signal amplitude of, for example, >40 mV (at 302, 303, 304) is indicative of a high quality signal, and in this case the threshold of, for example, 0.5 breaths/minute, may be set. For situations where the signal is lower in quality the threshold may be set to a more tolerant limit, such as for example, 1.5 breaths/minute, for the allowed respiration rate variability. Such a process (at 302) may employ a root means square (RMS) analysis of the current epoch.

The process then calculates and evaluates (at 305-308) a respiration rate range. For example, the respiration rate range may be determined by finding the minimum and maximum value of all the epochs' respiration rates between the CURRENT_EPOCH and the last epoch identified (e.g., labelled) as LIGHT_SLEEP. For example, if the last LIGHT_SLEEP was epoch N−6 with a rate of 14.2 BPM, and the epochs [N−5, N−4, N] had rates=[14.4, 14.8, 15.1, 14.9, 14.7, 14.6], then the breathing rate range is (15.1-14.4)=0.7 breaths/minute. If this BREATHING RATE RANGE is less than the stability threshold, then the current epoch is labelled as deep sleep (at 308) (which may optionally be represented with an "D" label). Alternatively, if the BREATHING RATE RANGE is larger than the stability threshold, then the current epoch is labelled as light sleep (at 307) (which may optionally be represented with an "L" label). Since very short sequences of DEEP_SLEEP are relatively uncommon, the algorithm also excludes (at 309, 310) cases where there is a run of four or less deep sleep epochs. This is done by checking the current sequence length of the DEEP_SLEEP prior epochs when a LIGHT_SLEEP epoch is encountered. If there are four or less preceding epochs of DEEP_SLEEP encountered since the last LIGHT_SLEEP epoch, these epoch labels are converted (at 310) to LIGHT_SLEEP. Since this condition makes it impossible to finish with DEEP_SLEEP count of less than 5, in such a case by default the algorithm accepts (at 311-313) the WAKE or SLEEP labels for the last four epochs (with SLEEP automatically treated as LIGHT_SLEEP).

As a further optional refinement of the embodiment described above, the stability threshold for "stable breathing" can be refined on a per-subject basis. For example, the default analysis may use a stability threshold of 0.5 breaths/minute, but if this threshold produces physiologically unreasonable values for deep sleep duration (e.g., >40% or less <5%), the threshold could be adaptively modified to a more suitable value.

An alternative embodiment that determines sleep stage based on respiration rate variability and amplitude is shown in FIG. 11. This process is based on the observation that the variability of the respiration rate and amplitude can serve to distinguish REM sleep. A period of relatively high variation of the breathing rate is considered as an indication of a REM sleep period. A period of relatively low variation of the breathing rate is considered to be associated with a state of deep sleep. One embodiment for assessing the variability of a time series is the approximate entropy. The approximate entropy assumes lower values for predictable time-series, and higher values as the time-sequence becomes more variable. In this embodiment, the signal 200 (e.g., raw movement signal) is input to a respiration analysis block 501. This respiration analysis block outputs a continuous respiration rate and respiration amplitude estimate (sample graphs of the outputs are illustrated in FIG. 12), e.g., on a 1-second timescale.

The respiration rate is then input into two processing blocks (at 502, 503) in segments (typically of duration 5 minutes, e.g., 300 samples of the respiration rate will be passed into the blocks labelled "Approximate Entropy Block" 502 and the "Power Spectral Density" 503). The approximate entropy is a known technique that assesses the predictability of a signal (i.e., variability) and is described, for example, in http://en.wikipedia.org/wiki/Approximate_entropy. The block will output a single number for each 5 minute epoch entered, which is the approximate entropy of that section of the signal. For example, the approximate entropy of five-minute segments of respiration rate can be calculated at 502, for example, using parameters of m=2 and m=3 for the embedding dimensions, and a value of r equal to 0.2. The power spectral density (PSD) processing block 503 will estimate the power spectral density of the respiration rate, such as by implementing a suitable technique (e.g., Welch's averaged periodogram, see http.//en.wikipedia.org/wiki/Welch's_method). The PSD estimate at 503 may generate three measurements: the slope of the PSD, the normalised high frequency power of the respiration rate variability and the low-frequency power of the respiration rate variability. The respiration amplitude signal may also be input to a power spectral density processing block (e.g., at 503) and will output a Low Frequency (LF) power estimate. The values calculated from the processing blocks (at 502,503 and 504) will be input to a classifier. The classifier may then combine them to produce a number which is then used to estimate a sleep stage as Deep, Light Sleep or REM. For example, number may be internal to the classifier (e.g., generated by it) and may be a discriminant value. In some cases, a combination of values within the classifier may be done in a linear fashion. For example, the discriminant value may be a linear weighted combination of the values output from blocks 502-504. In some cases, the value generated by the classifier may be a more complex non-linear combination (such as a value derived by combining the squared values of the values output from 502-504). The classifier may then generate a suitable Sleep Label (e.g., drawn from N1,N2,N3, REM or W) therefrom.

In some cases, detrended fluctuation analysis may be implemented to evaluate the short-term and long-term correlations of the respiration rate. Such a processing block may serve as an alternate to the power spectral density processing of the respiration rate that may also be implemented to capture the short-term and long-term correlations. Processing by detrended fluctuation analysis may be implemented by the methodology described in "Establishing the relation between detrended fluctuation analysis and power spectral density analysis for stochastic processes," Phys Rev E Stat Phys Plasmas Fluids Relat Interdiscip Topics. 2000 November; 62(5 Pt A):6103-10, by Heneghan and McDarby.

FIG. 12 illustrates an example of the respiration rate signal and the normalized respiration amplitude signals that may be generated by the respiration analysis processing block of FIG. 11. The respiration rate signal is shown in the top graph of FIG. 12. The missing periods (discontinuity) of the signal indicate that the signal quality was insufficient during the discontinuity for a reliable respiration rate estimate. The normalized respiration amplitude signal is illustrated in the bottom graph of FIG. 12. It also has discontinuity periods in the signal indicating where the signal quality is insufficient for a reliable respiration amplitude estimate. In some versions, the respiration rate amplitude signal may be obtained by filtering the raw signal 200 into a respiration rate range signal and then applying a Hilbert transform. Alternatively, it may be taken from the amplitude of the peak in respiration rate estimation such as with peak detection and/or envelope detection processing techniques.

FIG. 13 illustrates some of the intermediate processing previously described with reference to the processing components of FIG. 11. In the upper graph of FIG. 13, a power spectral density estimate of a segment of 5-minutes of respiration rate is plotted on a log-log plot. In block 502, data of the respiration rate signal may be processed to fit a line thereto (illustrated as the line labelled "LA" in the upper graph of FIG. 13) for detecting the slope, and the slope data of this fitted line is then output from the processing block. This is based on physiological observations of the long-term and short term control of respiration variability (see Rostig S; Kantelhardt J W; Penzel T et al. "Nonrandom variability of respiration during sleep in healthy humans." SLEEP 2005; 28(4):411-17.) In the lower graph of FIG. 13, the power spectral density of five minutes of respiration rate is illustrated on a semi-log scale. Power is represented at different frequencies. The "HIGH FREQUENCY" (labelled as "HF") power of the respiration rate variability may be determined with the integral of the PSD from 0.1 to 0.5 Hz. This may be normalised by dividing by the entire power of the signal. The "LOW-FREQUENCY" (shown as "LF") power may be defined as the power between 0 and 0.1 Hz.

A schematic representation of a scaled version of the numbered output (e.g., discriminant value) of the classifier block 505 of FIG. 11 is shown in FIG. 14. The smoother uninterrupted line represents a scaled version of the numbered output (labelled as "NO"). The breathing rate (labelled as "BR") is visualised by the more variable line in the image. A threshold value (labelled as "THLD") may be compared with the numbered output for classifying the sleep during a specific period. An example of such a value is illustrated by the straight horizontal line crossing the breathing rate axis slightly below the value of 13 breaths per minute. If the classifier block numbered output for the period is above the predetermined threshold value, the respective period may be classified as a REM sleep period. Alternatively, if the classifier block output for the period is below the predetermined threshold value, the respective period may be classified as period of deep sleep. This may be an alternative way of classifying a period as a deep sleep to that described with reference to FIG. 10 but may optionally also serve as an additional/combined test therewith for detecting REM and/or deep sleep.

FIG. 15 illustrates a display of the time course of the sleep stages to a user, which may optionally employ color-coded or shaded bars (e.g., vertical). In the example, bars extending above the main axis (representing time) may be taken as an indication of a state of wake. Bars extending below the axis may be taken as an indication of a sleep state. The amplitude of the bars may correspond to the stage of sleep. For example, the shortest bars may be taken as indicating light sleep, the medium length bars may be taken as indicating deep sleep and the longest bars may be taken as indicating a REM sleep.

FIG. 16 illustrates further processes of another example sleep stage monitoring apparatus 100 of the present technology. In this example, a sensor 1601 or sensors, such as the sensors previously described and including a non-contact sensor, generate(s) a plurality of signals. For example, the sensor of a monitor device (e.g., bed side device or respiratory treatment device) may produce four signals corresponding to a user proximate to the sensor. In the example, two signals may be representative of user motion and two may be representative of user breathing. Data thereof may be generated from each of the four signal channels by sampling (e.g., at 64 Hz or other suitable sampling rate.)

The data signals of the sensor may then be input for processing by a window and channel selector 1602. In this processing, each of the breathing channels may be analysed for inband breathing power. Thus, the selector will determine for each channel inband breathing power. The selector will then select the channel with the greatest inband breathing power such as the greatest inband power for a particular epoch (e.g., 30 seconds or other preset length). The selector will then output a window of three epochs (e.g., 30 seconds each) from the selected channel with the window centered on the particular epoch chosen by the selector as a result of the assessment of breathing power. In one example, the inband breathing power assessment may be implemented by spectral analysis processing of each epoch at one or more frequencies attributable to respiration.

The windowed data from the selector may then be input for processing by a wavelet transformer 1604. For example, a discrete wavelet transform of depth 5 may be performed on the windowed epoch data. A suitable filter bank for this process may be chosen. For example, the Biorthogonal 6.8 (bior6.8) wavelet may be implemented. Such a filter bank can be chosen such that the associated wavelet approximates a breath cycle. In such a case, the filters associated with the filter bank may be symmetrical (and so are linear phase). The analysis and synthesis filters may be approximately the same length and are long enough to ensure the wavelet coefficients are smoothened out in the wavelet domain. A hardware implementation of such an algorithm/processing method is well understood. Another suitable wavelet filter bank may be any one typically implemented with fingerprint compression.

The transformed data output from the wavelet processing may then be input for processing by a wavelet details extractor 1606. In this process, the wavelet details coefficients are extracted and reconstructed at the highest levels of the wavelet transform. These details can reveal what parts of the three epoch window (e.g., 90 second period) have high energy. Such high energy may be associated with parts of the signal that could have a lot of motion noise in them.

The extracted details coefficients are then input to a mask constructor 1608. In this process, a binary mask is constructed using the wavelet details. For example, the root mean square ("RMS") average of the power per sample may be calculated. If the power in any sample is significantly greater than the average power per sample over that windowed interval (e.g., 90 second interval) then that part of the binary mask is set to zero (0) otherwise the mask value for that sample is set to one (1). Lone or isolated ones (e.g., 010) and zeros (e.g., 101) are then smoothened out from the mask by inverting them.

This binary mask then serves as a map for determining which parts of the signal should be analysed versus which are the parts of the signal that contain a lot of noise.

The transformed data output from the wavelet processing may also be input for processing by a wavelet de-noiser 1610. This processes the transformed data to de-noise the signal. For example, the process may threshold the wavelet coefficients across all levels of wavelet decomposition and then reconstruct the signal. In one such version, a global thresholding mechanism may be implemented which is designed around a percentage of the power of the windowed signal.

The binary mask and de-noised signal are then input to a mask signal applier 1612. In the processing of the mask signal applier, the binary signal mask is examined to evaluate the de-noised signal. The evaluation identifies the longest portion of the de-noised signal that is greater than a desired length (e.g., 30 seconds). The identified portion of the de-noised signal is then output for feature extraction.

The de-noised wavelet signal from the de-noiser 1610 and the identified portion of the de-noised wavelet signal from the mask signal applier 1612 are then output to a wavelet feature extractor 1614. The processing of the extractor determines one or more features from the portion of the de-noised wavelet signal. For example, power in the highest wavelet details (e.g., the band just above the breathing band) is calculated. Similarly, power in the approximation coefficients may be calculated. The extracted features are then output to the sleep stage classifier 1622.

The denoised wavelet signal may also be input for processing by a breath analyzer 1615. Such processing may include detection of peaks and zero crossings such as with a peak and crossing detector 1616. For example, the processing of the peak and crossing detector 1616 may include extracting zero crossings of the signal. Additionally, a maximum and minimum for each pair of contiguous zero crossings may be calculated. With extracted data from the peak and crossing detector, the breath analyzer 1615 may further process the input data to extract breath interval and amplitude in an interval and amplitude detector 1618. For example, using the zero crossings and peaks, the breath interval is calculated and amplitude for each breath in the given window. Finally, with the breath interval and amplitude, breath statistics may be determined in a breath statistic calculator 1620. For example, such statistics on the breath interval and amplitude measurements from the given window may include the mean and/or variation. Other suitable breath metrics may also be calculated. Such a metric(s) for the input window can serve as a feature(s) for determining sleep stage of the given epoch (e.g., 30 second). As such, the metrics may be output to the sleep stage classifier 1622.

The sleep stage classifier 1622 thus processes the input features (e.g., wavelet features and breath features) to detect a sleep stage. For example, such a classifier may be a rule based processing system that classifies the input parameters. In some cases, the classifier may include input from a function library 1624 for sleep stage detection. The library may provide signal processing on one or more sensed signals to estimate movement, activity count and respiration rates on an epoch basis such as by using non-wavelet based processing. An example of such processing is described in International Patent Publication No. WO2007/143535 (Heneghan et al), the entire disclosure of which is incorporated herein by reference.

In some cases, the sleep stage classifier 1622 may include a Linear Discriminant Analysis (LDA) system. A rule based system may then identify key discriminating parameters for the LDA.

In some cases, the sleep stage data output from the sleep stage classifier 1622 may be further input to a pattern detector 1628. The pattern detector may process the sleep stage data, such as all of the data for a given night (e.g., a plurality of epochs) to perform pattern and trend analysis. The analysis may serve to remove any clearly errant classifications. For example, such pattern analysis may detect and correct a consecutive three epoch designation of wake, rem and wake (WRW) to remove or reclassify the middle rem epoch.

Generally, the processing steps illustrated by all the elements 1602-1628 in FIG. 16 are implemented in one or more processors that may be located in one or more devices, at least one of which may be a bedside unit, a portable mobile device located in the vicinity of the user or a server located remotely from the user.

Optionally, the final output may be generated as a hypnogram for the four sleep stages of wake, light, deep and REM sleep stages and may be presented to a user on a suitable display. By way of further example, the output may be generated in a chart format as illustrated in FIG. 15. In some cases, an absent state (i.e., no person present) may also be determined by BSP sleep wake library and output by the monitor.

Glossary

For the purposes of the present technology disclosure, in certain forms of the present technology, one or more of the following definitions may apply. In other forms of the present technology, alternative definitions may apply.

5.6.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.6.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

5.6.3 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow?.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peakflow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

5.6.4 PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Noise, conducted: (how measured, typical values)

Noise, transmitted: (how measured, typical values)

Pressure: Force per unit area. Pressure may be measured in a range of units, including $cmH_2O$, $g$-$f/cm^2$, hectopascal. 1 $cmH_2O$ is equal to 1 $g$-$f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

SoundPressure: The local deviation from ambient pressure at a given time instant as a result of a sound wave travelling through a medium. Sound power is usually given in decibels SPL, that is, decibels relative to a reference

5.6.5 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

5.6.6 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A method in a controller of a flow generator of respiratory therapy apparatus that is configured to generate a respiratory therapy, the method of the controller comprising:
    accessing one or more detected signals comprising movement components of a subject, the movement components including a bodily movement component and a respiration movement component, the one or more detected signals generated by one or more flow sensors;
    analysing at least a portion of the detected signals to calculate respiration variability, the respiration variability comprising one or more of variability of respiration rate and variability of respiration amplitude, the analysing including setting a respiration rate stability threshold value depending on a comparison of the variability of a measured respiratory rate signal with a respiration rate threshold value;
    generating an indication of sleep stage based on combining the respiration variability and the bodily movement component;
    executing a therapy parameter determination process that receives, as input, the generated sleep stage indication; and
    setting a treatment operation of the flow generator with an output of the therapy parameter determination process, the setting of the treatment operation being based, at least in part, on the generated sleep stage indication.

2. The method of claim 1, wherein the bodily movement component comprises one or more general bodily movements comprising turning over, twitching and adjusting position.

3. The method of claim 1, wherein the therapy parameter determination process receives further input comprising one or more of a measure of ventilation, a measure of inspiratory flow limitation, a measure of a presence of apnea and/or hypopnea, and a measure of a presence of snore.

4. The method of claim 1, wherein the therapy parameter determination process determines a treatment pressure as a function of the sleep stage.

5. The method of claim 4, wherein the therapy parameter determination process determines the treatment pressure as a function of measures of one or more of flow limitation, apnea, hypopnea, sleep stage and snore.

6. The method of claim 4, wherein the therapy parameter determination process determines the treatment pressure based on a target ventilation from a target ventilation determination process.

7. The method of claim 1, wherein the one or more detected signals further comprise one or more signals generated by one or more non-contact sensors that are configured to transmit sensing waves towards the subject.

8. The method of claim 7, wherein the one or more non-contact sensors receive a reflected radio-frequency signal from the subject to generate the one or more detected signals.

9. The method of claim 7, wherein the one or more non-contact sensors comprise an ultrasonic sensor.

10. The method of claim 7, wherein a sensor of the one or more non-contact sensors comprises a monitor device producing a plurality of signals corresponding to a user who is proximate to the sensor, wherein two of the signals are representative of user motion and two of the signals are representative of user breathing.

11. The method of claim 10, wherein the controller processes the signals that are representative of user breathing by spectral analysis to determine inband breathing power for each signal.

12. The method of claim 1, wherein the controller provides feedback to the subject comprising a sequence of the indications of sleep stages over a night.

13. The method of claim 12, wherein the feedback is in real time and controls one or more environmental factors comprising one or more of ambient temperature, ambient light level, ambient noise and ambient odour.

14. The method of claim 12, wherein the feedback controls an electronic device comprising a radio, a television or an entertainment device.

15. The method of claim 1, further comprising detection of a presence or absence of a person.

16. The method of claim 1, further comprising generating an estimate of power spectral density and calculating respiration rate with the estimate of power spectral density.

17. The method of claim 1, further comprising, in the controller, evaluating short-term and long-term correlations of respiration rate by detrended fluctuation analysis.

18. The method of claim 1, wherein the generating of the indication of sleep stage comprises identifying an epoch of deep sleep to distinguish it from other epochs of sleep or wake.

19. The method of claim 1, wherein the analysing comprises calculating a respiration rate range for each of a number of epochs,
comparing each calculated respiration range with the set respiration rate stability threshold value; and
classifying the epoch as a deep sleep if the calculated respiration range is smaller than the set respiration rate stability threshold value, or otherwise classifying the epoch as light sleep.

20. The method of claim 1, further comprising adjusting the respiration rate stability threshold value based on estimating signal quality of an input movement signal from a movement sensor.

21. The method of claim 1, wherein the method comprises classifying periods of sleep as either deep sleep or REM sleep on a basis of the variability of respiration rate during the period.

22. The method of claim 21, wherein a period of relatively high variation of respiration rate is considered as an indication of a REM sleep period, and a period of relatively low variation of respiration rate is considered to be associated with a state of deep sleep.

23. The method of claim 1, further comprising extracting breath statistics from a transformed signal, the transformed signal being transformed from the one or more detected signals.

24. The method of claim 23 wherein the extracted breath statistics comprise one or more of a mean of breath interval, a mean of breath amplitude, variation of breath interval and variation of breath amplitude.

25. The method of claim 1, wherein the indication of sleep stage comprises a series of indications for a plurality of epochs, the series of indications comprising two or more of: a wake stage, a light sleep stage, a deep sleep stage and a rem sleep stage.

26. The method of claim 1, further comprising generating signals indicative of movement to generate the indication of sleep stage with one or more of a respiratory inductance plethysmography sensor, pressure sensors embedded in a sensor film, a sensor mattress, a bioimpedance measurement system, an end-tidal CO2 respiratory monitor, and an optical sensor.

27. The method of claim 1, wherein a breath analyzer of the controller detects peaks and zero crossings in an input signal.

28. The method of claim 27, wherein the breath analyzer determines breath interval and amplitude for each breath.

29. Apparatus for generating a respiratory therapy for a subject comprising:
a flow generator configured to generate a respiratory therapy;
a controller configured to control operation of the flow generator; and
one or more flow sensors configured to generate one or more signals comprising movement components of a subject, the movement components including a bodily movement component and respiration component;
wherein the controller comprises a processor configured to:
access the one or more generated signals;
analyse at least a portion of the one or more generated signals to calculate respiration variability, the respiration variability comprising one or more of variability of respiration rate and variability of respiration amplitude, the analysis including setting a respiration rate stability threshold value depending on a comparison of the respiration variability with a respiration rate threshold value;
generate an indication of sleep stage based on combining the respiration variability and the bodily movement component;
execute a therapy parameter determination process that receives, as input, the generated sleep stage indication; and
set a treatment operation of the flow generator with an output of the therapy parameter determination process, the setting of the treatment operation being based, at least in part, on the generated sleep stage indication.

30. The apparatus of claim 29, wherein the bodily movement component represents one or more general bodily movements comprising turning over, twitching and adjusting position.

31. The apparatus of claim 29, wherein the therapy parameter determination process is configured to receive further input comprising one or more of a measure of ventilation, a measure of inspiratory flow limitation, a measure of a presence of apnea and/or hypopnea; and a measure of a presence of snore.

32. The apparatus of claim 29, wherein the therapy parameter determination process is configured to determine a treatment pressure as a function of the sleep stage.

33. The apparatus of claim 32, wherein the therapy parameter determination process is configured to determine the treatment pressure as a function of measures of one or more of flow limitation, apnea, hypopnea, sleep stage and snore.

34. The apparatus of claim 32, wherein the therapy parameter determination process is configured to determine the treatment pressure based on a target ventilation from a target ventilation determination process.

35. The apparatus of claim 29, wherein the one or more generated signals further include on or more signals generated by one or more non-contact sensors that are configured to transmit sensing waves towards the subject.

36. The apparatus of claim 35, wherein the one or more non-contact sensors receive a reflected radio-frequency signal from the subject to generate the one or more generated signals.

37. The apparatus of claim 35, wherein the one or more non-contact sensors comprise an ultrasonic sensor.

38. The apparatus of claim 35, wherein a sensor of the one or more non-contact sensors comprises a monitor device producing a plurality of signals corresponding to a user who is proximate to the sensor, wherein two of the signals are representative of user motion and two of the signals are representative of user breathing.

39. The apparatus of claim 38, wherein the controller is configured to process the signals that are representative of user breathing by spectral analysis to determine inband breathing power for each signal.

40. The apparatus of claim 29, wherein the controller is configured to provide feedback to the subject comprising a sequence of the indications of sleep stages over a night.

41. The apparatus of claim 40, wherein the feedback is in real time and controls one or more environmental factors comprising one or more of ambient temperature, ambient light level, ambient noise and ambient odour.

42. The apparatus of claim 40, wherein the feedback controls an electronic device comprising a radio, a television or an entertainment device.

43. The apparatus of claim 29, wherein the controller is further configured to detect a presence or absence of a person.

44. The apparatus of claim 29, wherein the controller is configured to generate an estimate of power spectral density and calculating respiration rate with the estimate of power spectral density.

45. The apparatus of claim 29, wherein the controller is configured to evaluate short-term and long-term correlations of respiration rate by detrended fluctuation analysis.

46. The apparatus of claim 29, wherein to generate the indication of sleep stage, the controller is configured to identify an epoch of deep sleep to distinguish it from other epochs of sleep or wake.

47. The apparatus of claim 29, wherein to analyse the generated signals, the controller is further configured to:
- calculate a respiration rate range for each of a number of epochs,
- compare each calculated respiration range with the set respiration rate stability threshold value; and
- classify the epoch as a deep sleep if the calculated respiration range is smaller than the set respiration rate stability threshold value, or otherwise classifying the epoch as light sleep.

48. The apparatus of claim 29, wherein the controller is further configured to adjust the respiration rate stability threshold value based on estimating signal quality of an input movement signal from a movement sensor.

49. The apparatus of claim 29, wherein the controller is configured to classify periods of sleep as either deep sleep or REM sleep on a basis of the variability of respiration rate during the period.

50. The apparatus of claim 49, wherein a period of relatively high variation of respiration rate is considered as an indication of an REM sleep period, and a period of relatively low variation of respiration rate is considered to be associated with a state of deep sleep.

51. The apparatus of claim 29, wherein the controller is configured to extract breath statistics from a transformed signal, the transformed signal being transformed from the one or more generated signals.

52. The apparatus of claim 51 wherein the extracted breath statistics comprise one or more of a mean of breath interval, a mean of breath amplitude, variation of breath interval and variation of breath amplitude.

53. The apparatus of claim 29, wherein the indication of sleep stage comprises a series of indications for a plurality of epochs, the series of indications comprising two or more of: a wake stage, a light sleep stage, a deep sleep stage and a rem sleep stage.

54. The apparatus of claim 29, wherein the apparatus is further configured to generate signals indicative of movement to generate the indication of sleep stage with one or more of a respiratory inductance plethysmography sensor, pressure sensors embedded in a sensor film, a sensor mattress, a bioimpedance measurement system, and an end-tidal $CO_2$ respiratory monitor, and an optical sensor.

55. The apparatus of claim 29, wherein a breath analyzer of the controller is configured to detect peaks and zero crossings in an input signal.

56. The apparatus of claim 55, wherein the breath analyzer is configured to determine breath interval and amplitude for each breath.

* * * * *